United States Patent [19]
Kaniewski et al.

[11] Patent Number: 6,015,940
[45] Date of Patent: Jan. 18, 2000

[54] VIRUS RESISTANT POTATO PLANTS

[75] Inventors: Wojciech Kazimierz Kaniewski, Chesterfield; Jennifer Katherine Lodge, St. Louis; Nilgun Ereken Tumer, Chesterfield, all of Mo.

[73] Assignee: Monsanto Company, St. Louis, Mo.

[21] Appl. No.: 07/865,169

[22] Filed: Apr. 7, 1992

[51] Int. Cl.[7] ............................ C12N 15/29; C12N 15/62; C12N 15/82; A01H 5/00; A01H 5/06

[52] U.S. Cl. ...................... 800/279; 800/317.2; 435/69.1; 435/69.7; 435/69.8; 435/468; 536/23.6

[58] Field of Search ...................... 800/205, 279, 800/317.2; 435/172.3, 69.1, 69.7, 69.8, 468; 536/23.6

[56] References Cited
PUBLICATIONS

Lawson, C., et al. Bio/Technology, vol. 8, (1990) pp. 127–134.
Lodge, J., et al. J. of Cellular Biochemistry, vol. 14E (1990), p. 304.
Ready, M.P., et al. PNAS, vol. 83 (1986) pp. 5053–5056.
Stockhaus, J., et al. PNAS, vol. 84 (1987) pp. 7943–7947.
Twell, D., et al. Plant Mol. Biol., vol. 9 (1987) pp. 365–375.
Bevan, M., et al. EMBO Journal, vol. 8 (1989) pp. 1899–1906.

*Primary Examiner*—David T. Fox

[57] ABSTRACT

Potato plants and tubers that express a pokeweed antiviral protein and are thereby rendered resistant to infection by at least one of PVX and PVY and a method therefore are disclosed. A variant DNA sequence for the spring leaf form of pokeweed antiviral protein is also disclosed.

20 Claims, 15 Drawing Sheets

```
PAP-S   INTITFDAG (H) ATINKYATFMESL?NEAKD
PAP II   N IVFDVE N ATPETYSNFLTSLR EAVKD
PAP     VNTIIYNVG S TTISFYATFLNDLRNEAKDP
PAP'    VNTIIYNVG S TTISKYATFLDNLRNEAKDP
```

FIGURE 1

```
PAP´            V   N   T   I   I   Y   N   V   G   S   T   T   I   S   F
               5'---------PAPPCR------------3´
DNA         5´ GUN AAY ACN ATH ATH TAY AAY GTN GGN TCN ACN ACN ATH ACN WWN
               CAN TTR TGN TAB TAB ATR TTR CAN CCN AGN TGN TGN TAB TGN SSN aa      Y   A   T   F   L   D   N   L   R   N   E   A   K   D   P   S   L
DNA    UAY GCN ACN UUY YUN RAY RAY YUN TGN AAY GAR GCM AAR GAY CCM AGU YUN
       ATR CGN TGN AAR RAN YTR YTR RAN RCN TTR CTY CGN TTY CTR GGN TCR RTN
                                           3'-----PA3SPRING-----5´
```

```
CTATGAAGTC GGGTCAAAGC ATATACAGGC TATGCATTGT TAGAAACATT GATGCCTCTG 60
ATCCCGATAA ACAATACAAA TTAGACAATA AGATGACATA CAAGTACCTA AACTGTGTAT 120
GGGGGAGTGA AACCTCAGCT GCTAAAAAA CGTTGTAAGA AAAAAGAAA GTTGTGAGTT 180
AACTACAGGG CGAAAGTATT GGAACTAGCT AGTAGGAAGG GAAGATGAAG TCGATGCTTG 240
TGGTGACAAT ATCAATATGG CTCATTCTTG CACCAACTTC AACTTGGGCT GTGAATACAA 300
TCATCTACAA TGTTGGAAGT ACCACCATTA GCAAATACGC CACTTTTCTG AATGATCTTC 360
GTAATGAAGC GAAAGATCCA AGTTTAAAAT GCTATGGAAT ACCAATGCTG CCCAATACAA 420
ATACAAATCC AAAGTACGTG TTGGTTGAGC TCCAAGGTTC AAATAAAAAA ACCATCACAC 480
TAATGCTGAG ACGAAACAAT TTGTATGTGA TGGGTTATTC TGATCCCTTT GAAACCAATA 540
AATGTCGTTA CCATATCTTT AATGATATCT CAGGTACTGA ACGCCAAGAT GTAGAGACTA 600
CTCTTTGCCC AAATGCCAAT TCTCGTGTTA GTAAAAACAT AAACTTTGAT AGTCGATATC 660
CAACATTGGA ATCAAAAGCG GGAGTAAAAT CAAGAAGTCA GGTCCAACTG GGAATTCAAA 720
TACTCGACAG TAATATTGGA AAGATTTCTG GAGTGATGTC ATTCACTGAG AAAACCGAAG 780
CCGAATTCCT ATTGGTAGCC ATACAAATGG TATCAGAGGC AGCAAGATTC AAGTACATAG 840
AGAATCAGGT GAAAACTAAT TTTAACAGAG CATTCAACCC TAATCCCAAA GTACTTAATT 900
TGCAAGAGAC ATGGGGTAAG ATTTCAACAG CAATTCATGA TGCCAAGAAT GGAGTTTTAC 960
CCAAACCTCT CGAGCTAGTG GATGCCAGTG GTGCCAAGTG GATAGTGTTG AGAGTGGATG
1020
AAATCAAGCC TGATGTAGCA CTCTTAAACT ACGTTGGTGG GAGCTGTCAG ACAACTTATA
1080
ACCAAAATGC CATGTTTCCT CAACTTATAA TGTCTACTTA TTATAATTAC ATGGTTAATC
1140
TTGGTGATCT ATTTGAAGGA TTCTGATCAT AAACATAATA AGGAGTATAT ATATATTACT
1200
CCAACTATAT TATAAAGCTT AAATAAGAGG CCGTGTTAAT TAGTACTTGT TGCCTTTTGC
1260
TTTATGGTGT TGTTTATTAT GCCTTGTATG CTTGTAATAT TATCTAGAGA ACAAGATGTA
1320
CTGTGTAATA GTCTTGTTTG AAATAAAACT TCCAATTATG ATGCAAAAAA AAAAAAAA
1379
```

FIGURE 4

```
CTATGAAGTC GGGTCAAAGC ATATACAGGC TATGCATTGT TAGAAACATT GATGCCTCTG 60

ATCCCGATAA ACAATACAAA TTAGACAATA AGATGACATA CAAGTACCTA AACTGTGTAT 120

GGGGGAGTGA AACCTCAGCT GCTAAAAAAA CGTTGTAAGA AAAAAGAAA GTTGTGAGTT 180

AACTACAGGG CGAAAGTATT GGAACTAGCT AGTAGGAAGG GAAGATGAAG TCAATGCTTG 240

TGGTGACAAT ATCAATATGG CTCATTCTTG CACCAACTTC AACTTGGGCT GTGAATACAA 300

TCATCTACAA TGTTGGAAGT ACCACCATTA GCAAATACGC CACTTTTCGG AATGATCTTC 360

GTAATGAAGC GAAAGATCCA AGTTTAAAAT GCTATGGAAT ACCAATGCTG CCCAATACAA 420

ATACAAATCC AAAGCACGTG TTGGTTGAGC TCCAAGGTTC AAATAAAAAA ACCATCACAC 480

TAATGCTGAG ACGAAACAAT TTGTATGTGA TGGGTTATTC TGATCCCTTT GAAACCAATA 540

AATGTCGTTA CCATATCTTT AATGATATCT CAGGTACTGA ACGCCAAGAT GTAGAGACTA 600

CTCTTTGCCC AAATGCCAAT TCTCGTGTTA GTAAAAACAT AAACTTTGAT AGTCGATATC 660

CAACATTGGA ATCAAAAGCG GGAGTAAAAT CAAGAAGTCA GGTCCAACTG GAATTCAAA 720

TACTCGACAG TAATATTGGA AAGATTTCTG GAGTGATGTC ATTCACTGAG AAAACCGAAG 780

CCGAATTCCT ATTGGTAGCC ATACAAATGG TATCAGAGGC AGCAAGATTC AAGTACATAG 840

AGAATCAGGT GAAAACTAAT TTTAACAGAG CATTCAACCC TAATCCCAAA GTACTTAATT 900

TGCAAGAGAC ATGGGGTAAG ATTTCAACAG CAATTCATGA TGCCAAGAAT GGAGTTTTAC 960

CCAAACCTCT CGAGCTAGTG GATGCCAGTG GTGCCAAGTG GATAGTGTTG AGAGTGGATG
1020
AAATCAAGCC TGATGTAGCA CTCTTAAACT ACGTTGGTGG GAGCTGTCAG ACAACTTATA
1080
ACCAAAATGC CATGTTTCCT CAACTTATAA TGTCTACTTA TTATAATTAC ATGGTTAATC
1140
TTGGTGATCT ATTTGAAGGA TTCTGATCAT AAACATAATA AGGAGTATAT ATATATTACT
1200
CCAACTATAT TATAAAGCTT AAATAAGAGG CCGTGTTAAT TAGTACTTGT TGCCTTTTGC
1260
TTTATGGTGT TGTTTATTAT GCCTTGTATG CTTGTAATAT TATCTAGAGA ACAAGATGTA
1320
CTGTGTAATA GTCTTGTTTG AAATAAAACT TCCAATTATG ATGCAAAAAA AAAAAAAA
1379
```

FIGURE 5

```
TCATCAAAAT ATTTAGCAGC ATTCCAGATT GGGTTCAATC AACAAGGTAC GAGCCATATC  60
ACTTTATTCA AATTGGTATC GCCAAAACCA AGAAGGAACT CCCATCCTCA AAGGTTTGTA 120
AGGAAGAATT CTCAGTCCAA AGCCTCAACA AGGTCAGGGT ACAGAGTCTC CAAACCATTA 180
GCCAAAAGCT ACAGGAGATC AATGAAGAAT CTTCAATCAA AGTAAACTAC TGTTCCAGCA 240
CATGCATCAT GGTCAGTAAG TTTCAGAAAA AGACATCCAC CGAAGACTTA AAGTTAGTGG 300
GCATCTTTGA AAGTAATCTT GTCAACATCG AGCAGCTGGC TTGTGGGGAC CAGACAAAAA 360
AGGAATGGTG CAGAATTGTT AGGCGCACCT ACCAAAAGCA TCTTTGCCTT TATTGCAAAG 420
ATAAAGCAGA TTCCTCTAGT ACAAGTGGGG AACAAAATAA CGTGGAAAAG AGCTGTCCTG 480
ACAGCCCACT CACTAATGCG TATGACGAAC GCAGTGACGA CCACAAAAGA ATTCCCTCTA 540
TATAAGAAGG CATTCATTCC CATTTGAAGG ATCATCAGAT ACTAACCAAT ATTTCTC    597
```

FIGURE 15

VIRUS RESISTANT POTATO PLANTS

FIELD OF THE INVENTION

This invention relates in general to transgenic plants, and more particularly to potato plants and tubers that are resistant to infection by potato virus X, potato virus Y and/or potato leafroll virus and which also exhibit insecticidal properties.

BACKGROUND OF THE INVENTION

Plant viruses are a continuing problem in the agricultural industry. Viral infection in plants causes a variety of undesirable effects including stunted growth, altered morphology, reduced yield, diminished quality and increased susceptibility to damage by other pests. The use of chemicals to control viruses is not always desirable and the use of biological agents, e.g. infection of plants with an attenuated strain of a virus, has not been always effective or desirable.

Damage to plants by insects is also a significant problem in agriculture. Crop yield can be significantly decreased and crop quality can be compromised if infested with insects. Control of insects can be obtained by insecticides, introduction of natural predators of the insect pest, crop rotation, or by genetic modification of plants to express an insect specific toxin.

Scientists have recently developed means to produce virus resistant plants using genetic engineering techniques. Such an approach is advantageous in that the means for providing the protection is incorporated in the plant itself and can be passed to its progeny. Most prominently, incorporation of a gene encoding the capsid protein (coat protein) of a plant virus in a plant has conferred resistance to the virus and related viruses. (Beachy et al. 1990). Even though coat-protein mediated viral resistance has proved to be useful in a variety of situations, it may not always be the most effective or most desirable means for providing viral resistance. In such instances, it would be advantageous to have other methods for conferring viral resistance in plants that also incorporate the advantages of a genetic engineering approach.

It has been suggested that pokeweed antiviral protein, an enzyme that is naturally expressed in pokeweed, functions as an antiviral defense mechanism in such plant. (Ready et al. 1986). This protein is one of a family of ribosome inhibiting proteins which inhibit translation by inactivating ribosomes. These proteins are potent ribosome inhibitors and are known to inactivate both homologous and heterologous plant ribosomes. (Schonfelder et al. 1990). Pokeweed antiviral protein is known to inhibit viral infection if applied exogenously to a plant surface or placed in direct contact with a virus. (Irwin et al. 1980; Tomlinson et al. 1974; Wyatt et al. 1969). Despite the antiviral function suggested for pokeweed antiviral protein in pokeweed and its exogenous effect, the pokeweed plant is itself still susceptible to infection by a variety of plant viruses including some potyviruses e.g. watermelon mosaic virus II and some potexviruses e.g. Hydrangea ringspot virus. (Klinkowski 1977) Therefore, the extent to which this protein is capable of providing protection against viral infection and which viruses it is capable of protecting against when expressed in planta was not known. This is especially true with respect to the expression of the protein in plants other than pokeweed. Furthermore, in pokeweed, the protein is found primarily sequestered in the cell walls and does not significantly inhibit the normal translation activities of the cell. (Ready et al. 1986) Whether pokeweed antiviral protein could be expressed in a plant other than pokeweed and not interrupt the normal translation activities of that plant was not known.

SUMMARY OF THE INVENTION

Potato plants and tubers expressing a heterologous gene which is capable of causing the expression of pokeweed antiviral protein in the plant or tuber at a level sufficient to confer resistance to the plant from infection by a virus selected from the group consisting of potato virus X (PVX) and potato virus Y (PVY) are provided. The potato plants and tubers may also be resistant to infection by potato leafroll virus (PLRV). The heterologous gene includes the necessary regulatory sequences to cause transcription and subsequent translation of a structural DNA sequence encoding pokeweed antiviral protein. The gene may also include a signal sequence which is capable of causing the translocation of the pokeweed antiviral protein to the potato or tuber cell walls.

A structural DNA sequence encoding a variant form of the instant pokeweed antiviral protein (PAP') and a chimeric gene including such DNA sequence with the necessary regulatory sequences to cause the expression of this protein in potato plants are also provided. The variant PAP' gene encodes an arginine at amino acid position 20 of the mature protein in place of the leucine encoded in the wild-type PAP' gene and a histidine encoded at amino acid position 49 of the mature protein in place of the tyrosine encoded in the wild-type PAP' gene. The variant PAP' gene, as well as a gene encoding a wild-type pokeweed antiviral protein in any of its various forms, can be expressed in potato plants or tubers to provide resistance to infection by at least one of PVX, PVY and PLRV and to also provide insecticidal properties.

BRIEF DESCRIPTION OF THE DRAWINGS

FIG. 1 shows the N-terminal amino acid sequence of various forms of the mature pokeweed antiviral protein which have been aligned to highlight homologous residues.

FIG. 2 shows the predicted N-terminal cDNA sequence of the PAP gene isolated and purified herein and the putative amino acid sequence corresponding thereto.

FIG. 4 shows the nucleotide sequence of the PAP' (pokeweed antiviral protein spring leaf form) cDNA from *Phytolacca americana*. (SEQ ID NO:1).

FIG. 5 shows the nucleotide sequence of a variant PAP' cDNA from *Phytolacca americana*. (SEQ ID NO:2).

FIG. 15 presents the DNA sequence of a FMV35S promoter. (SEQ ID NO:8).

DETAILED DESCRIPTION OF THE INVENTION

Figure 3:
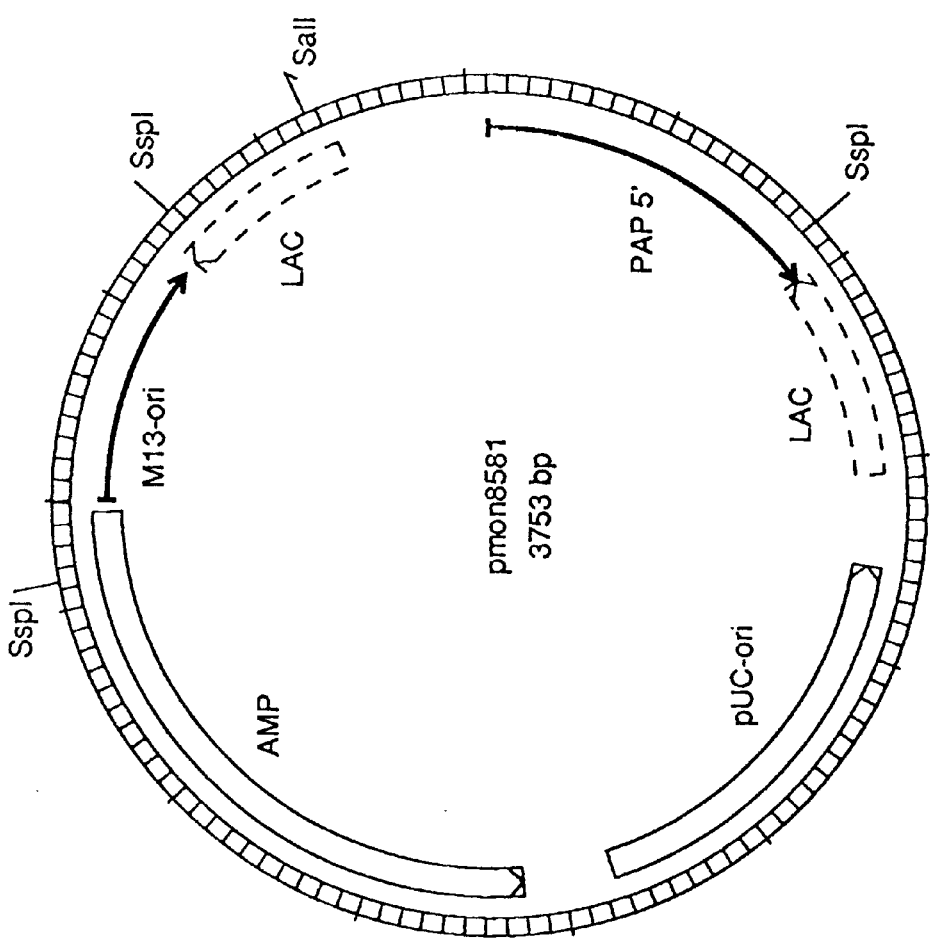
FIG. 3 shows the plasmid map of pMON8581.

The present invention provides a means and a method for protecting potato plants and tubers from virus infection and damage by insect pests by expressing a pokeweed antiviral protein in the plant or tuber. Various forms of pokeweed antiviral protein are known. PAP-S is the seed form of the protein, PAP is the spring leaf form of the protein, and PAP-II is the summer leaf form of the protein. The phrase "pokeweed antiviral protein" is used herein to generally denote any form of the protein. The purified protein can be obtained in its various forms commercially from Calbiochem or can be isolated from the seeds or leaves of pokeweed, *Phytolacca americana*, by known procedures. (Irwin et al. 1980).

As an exemplary embodiment of this invention, a spring leaf form of the protein, hereinafter referred to as PAP', was isolated and purified. Leaves were removed from a pokeweed plant and a crude extract made in 50 mM Tris-HCl buffer, pH 7.5. Ammonium sulfate was added to the extract to precipitate the protein and the precipitate resulting from the addition of between 40% and 100% saturation of ammonium sulfate was collected. The precipitate was resuspended in extraction buffer and dialyzed against extraction buffer to remove the ammonium sulfate. The dialyzed resuspension was adjusted to pH 6.5 and applied to a Mono S cation exchange column. The PAP' in the resuspension bound to the column and was eluted by the application of a linear gradient of a NaCl solution from 0 mM NaCl to 500 mM NaCl. The PAP' eluted as a single peak at about 100 mM NaCl. The fractions containing the purified PAP were pooled and used to determine the amino acid sequence of this protein and to test the in vitro antiviral activity of the PAP.

The first 30 amino acid residues of the purified mature PAP' were determined using standard methodology and compared to the published amino acid sequences for the various pokeweed forms of antiviral protein. The N-terminal amino acid sequences of PAP and PAP II have been published in Bjorn et al. (1984) and the PAP-S protein sequence has been published in Houston et al. (1983). The purified PAP' amino acid sequence showed only one major variance to the published sequence for PAP. At position 15, the purified sequence presented a lysine in place of the published phenylalanine residue. At positions 21 and 22, the two amino acids are the related asparagine and aspartic acid in both the purified and the published sequences, but in the opposite order. The mature protein starts with a valine residue which is the twenty-third residue from the first translation initiation codon. It is believed that the first 22 amino acids encode a signal sequence which translocates the protein to the cell wall and is subsequently cleaved. Thus, the first N-terminal amino acid of the protein is amino acid 23 of the entire gene.

FIG. 1 shows the first 30 N-terminal amino acids of the mature protein of the various forms of pokeweed antiviral protein which have been aligned to highlight homologous residues as in Bjorn et al. (1984). In this and all amino acid sequences to follow, the standard single letter nomenclature is used. All peptide structures represented in the following description are shown in conventional format wherein the amino group at the N-terminus appears to the left and the carboxyl group at the C-terminus at the right. An "X" is used when the amino acid residue is unknown and parentheses designate that an unambiguous assignment is not possible and the amino acid designation within the parentheses is the most probable estimate based on known information. FIG. 1 illustrates that there is a substantial degree of homology in the N-termini of the various forms of pokeweed antiviral protein as also determined by Bjorn et al. (1984) and Houston et al. (1983).

The antiviral activity of the various forms of pokeweed antiviral protein was determined by applying a solution of the desired form of the protein on the leaves of a plant while simultaneously mechanically inoculating the leaves with virus. Pokeweed antiviral protein forms PAP-S and PAP' were tested. Two young leaves of fifteen (15) *N. tobacum* cv. Samsun plants were mechanically inoculated with 50 μl/leaf of potato virus X (PVX) at a concentration of 1 μg/ml in 0.1M NaP (sodium phosphate) buffer pH7. Simultaneously, the same leaves were inoculated with either 50 μl of buffer alone, buffer containing 1 μg/ml of a commercial preparation of PAP-S, or 1 μg/ml of PAP purified from the Mono-S column fractions. The plants were scored visually for symptom development. At eight days post inoculation (8 dpi), 3 of 5 plants inoculated with PVX alone showed severe symptoms whereas all of the remaining plants were symptom-free. At 14 days post inoculation (14 dpi), the inoculated leaves were harvested and analyzed by ELISA for the presence of virus. Four of the five plants inoculated with PVX alone contained high levels of virus, but none of the plants inoculated with PVX and PAP' or PVX and PAP-S contained detectable virus. Thus, the antiviral activity of the various forms of pokeweed antiviral protein are similar when exogenously applied.

A DNA sequence encoding a pokeweed antiviral protein was cloned and isolated from a cDNA library made from RNA recovered from pokeweed leaves. The gene encoding a spring leaf form of pokeweed antiviral protein (PAP') was cloned for exemplary purposes. Those skilled in the art will recognize that the same or similar strategy can be utilized to isolate the genes encoding other forms of pokeweed antiviral protein.

The strategy for cloning the PAP' gene was to make a cDNA library from RNA isolated from leaves and identify a clone encoding PAP' using a fragment of DNA generated by polymerase chain reaction (PCR). To isolate RNA, young pokeweed leaves were harvested and pulverized in liquid nitrogen. To the pulverized leaves, one volume of phenol and two volumes of homogenization buffer containing 1% triisopropylnaphthalene sulfonic acid, 6% para-aminosalicylic acid, 100 mM Tris-HCl pH 7.6, 50 mM EGTA, 100 mM NaCl, 1% SDS and 50 mM β-mercaptoethanol were added. The mixture was homogenized for 3 minutes with a polytron and one volume of choloroform:isoamyl alcohol (24:1) was added. The mixture was slowly shaken at room temperature for 15 minutes and then centrifuged for 15 minutes at 6000 rpm in a GSA rotor. The supernatant was re-extracted with phenol:chloroform:isoamyl alcohol (25:24:1) and the aqueous phase collected. The nucleic acids in the mixture were precipitated by the addition of NaOAc (sodium acetate) to a final concentration of 0.3M and two volumes of ethanol. This mixture was maintained at −20° C. overnight. The precipitated nucleic acids were redissolved in water, treated with DEPC, and LiCl added to a final concentration of 2M to precipitate the RNA. This mixture was maintained at 4° C. overnight. The LiCl precipitations were repeated twice in smaller volumes to concentrate the RNA. Poly A+ RNA was isolated from the total RNA by passing the RNA over an oligo dT agarose column and eluting the poly A+ RNA with 10 mM Tris-HCl pH 7.8 and 1 mM EDTA. A cDNA library was prepared from this poly A+ RNA in a lambda derived cloning vector, lambda-zap, by the Stratagene Company.

A probe to identify the cDNA for PAP was made by amplifying the DNA that encodes the first 30 amino acids of the mature PAP using polymerase chain reaction (PCR). The template DNA for the PCR reaction was cDNA made from poly A+ RNA from pokeweed leaves using a "cDNA Synthesis System Plus" kit from Amhersham Company by following the manufacturer's instructions. The 5' primer, SEQ ID NO:3, was designed to match the sense strand of a putative DNA sequence encoding amino acids one through eight of PAP and the 3' primer, SEQ ID NO:4, was designed to match the antisense strand of amino acids 25 through 30 of PAP as shown in FIG. 2. In this and all nucleotide sequences, the standard nomenclature is used, where A=adenine, T=thymine, G=guanidine, C=cytosine, R=A or G, Y=C or T, H=A or C or T, and N=A or C or G or T. In particular, the 5' and 3' primers used were, respectively:

5'GGGGTCTAGAATTCGTNAAYACNATHATHTAYAAYGT
(SEQ ID NO:3); and

5'GGRTCYTTYGCYTCRTT (SEQ ID NO:4).

Approximately 10 ng of cDNA and 1 ng of each primer were added to the PCR mixture using the manufacturer's (Perkin-Elmer Cetus) instructions and buffers. The reaction was cycled as follows: 1 minute at 94° C., 2 minutes at 40° C., and 3 minutes at 72° C. for five cycles. This was followed by 30 cycles of 1 minute at 94° C., 2 minutes at 50° C. and 3 minutes at 72° C. A band of DNA of the expected size (approximately 100 bp) was observed on a 2% low melting agarose gel. This band was excised from the gel and radionucleotides were incorporated into the DNA in another PCR reaction which included 10 μl of the gel slice containing the DNA fragment, 10 μl of [$^{32}$P]-dCTP (Amhersham), 1 ng of the 5' primer, 1 ng of the 3' primer, 0.25 mM each of DATP, dGTP, TTP and 2.5 Units of Taq polymerase. This reaction was run for 10 cycles with a minute at 94° C. denaturation step, a 2 minute at 50° C. annealing step, and a 3 minute at 72° C. extension step. The labelled probe was purified on a G-25 spin column.

A clone of the PAP' gene was obtained from the cDNA library by probing the library with the labeled 100 bp PCR fragment according to the protocols supplied by Stratagene Company with the cDNA library. Ten thousand (10,000) phage particles were mixed with 0.6 ml of a fresh (O.D.$_{600}$=0.5) culture of BB4 E. coli cells (obtained from Stratagene) grown in LN broth supplemented with 0.2% maltose. Seven (7) ml of LN+0.7% agarose was added to this mixture and plated on a 150 mm plate containing LN+1.5% agar and incubated for six hours at 37° C. After chilling the plates at 4° C., the plaques were transferred to duplicate nitrocellulose filters. The phage were denatured by submerging the filters in 1.5M NaCl, 0.5M NaOH for 2 minutes, and then in 1.5M NaCl, 0.5M Tris-HCl, pH 8.0 for 2 minutes. The filters were rinsed in 0.2M Tris-HCl, pH 7.5, 2×SSC (0.15 MNaCl, 0.015M sodium citrate, pH 7.0), air dried and baked at 80° C. for 2 hours. The baked filters were wetted in 2×SSC for 5 minutes and prewashed in 6×SSC, 0.5% SDS and 1 mM EDTA for 30 minutes at 50° C. The filters were then treated overnight at 68° C. in a prehybuidization solution of 6×SSC, 0.5% SDS, 100 μg/ml sheared salmon sperm DNA, 50 μg/ml tRNA and 5× Denhardt's solution (5× is 0.1% Ficoll Type 400, 0.1% polyvinylpyrrolidone and 0.1% bovine serum albumin) using 8 ml for each filter. The prehybridization solution was poured off and replaced with hybridization solution; 6×SSC and 0.5% SDS, using 5 ml for each filter. The $^{32}$P labeled 100 bp PCR product was added as a probe at 2×10$^6$ cpm/filter. Hybridization was performed for 14 hours at 68° C. and the filters were then washed twice at 23° C. with 6×SSC, 0.2% SDS for 15 minutes and once at 68° C. and then exposed to film.

Several plaques which hybridized to the probe on each of the duplicate filters were picked for further analysis. One feature of the lambda-ZAP system is that a plasmid, which is easier to characterize, can be excised from the phage in vivo and this was done first. The plaques were cored from the master plate and transferred to 500 μl of SM buffer +20 μl chloroform in a microfuge. Two hundred (200) μl of the phage stock was added to 200 μl of OD$_{600}$=0.5 XL1-Blue cells (Stratagene) and 1 μl of R408 helper phage (Stratagene). This mixture was incubated for 15 minutes at 37° C., 5 ml of 2XYT media was added, and incubated for 6 hours at 37° C. The tube was heated to 70° C. for 5 minutes and centrifuged at 4000 g for 5 minutes. Two hundred (200) μl of the supernatant was added to 200 μl of OD$_{600}$=1.0 XL1-Blue cells and different amounts were plated on LB plates containing 100 μg/ml ampicillin.

The resultant colonies were screened for inserts which hybridized to the 100 bp PCR fragment by being patched onto duplicate LB-amp plates and grown for 8 hours. The patches were transferred to nitrocellulose filters and the filters were sequentially soaked on Whatman 3MM paper saturated with 10% SDS for 3 minutes, 0.5M NaOH for 5 minutes and finally on paper saturated with 0.5M sodium acetate for 5 minutes. The filters were then rinsed in 2×SSC, air dried for 30 minutes and baked at 80° C. for 2 hours. The baked filters were wetted in 2×SSC for 5 minutes and prewashed in 6×SSC, 0.5% SDS and 1 mM EDTA for 30 minutes at 50° C. Excess debris was removed with a chemwipe wetted in prewash solution. The filters were then treated overnight at 68° C. in a prehybridization solution of 6×SSC, 0.5% SDS, 100 μg/ml sheared salmon sperm DNA, 50 μg/ml tRNA and 5× Denhardt's solution using 10 ml for each filter. The prehybridization solution was poured off and replaced with hybridization solution; 6×SSC and 0.5% SDS, using 10 ml for each filter. The $^{32}$P labeled 100 bp PCR fragment was added as a probe at 2×10$^6$ cpm/filter. Hybridization was performed for 14 hours at 68° C. and the filters were washed twice at 23° C. with 6×SSC, 0.2% SDS for 15 minutes and once at 68° C. and then exposed to film.

Four plasmids, identified as pMON8581, pMON8582, pMON8583 and pMON8584, contained cDNAs that hybridized to the 100 bp PCR fragment and were analyzed by restriction digestion and sequencing. All DNA sequencing utilized the Sequenase 2.0 kit (International Biotechnologies Inc.) using the manufacturer's protocol. CsCl purified plasmid DNA was used as the sequencing template. One (1) μg of DNA in 7 μl of 10 mM Tris-HCl pH7.4, 1 mM EDTA (TE buffer) was denatured using 3 μl of 0.2M NaOH at room temperature for five minutes. The sequencing primer, supplied by the manufacturer, was added (0.25 pg of primer in 7 μl of TE), and the DNA precipitated by the addition of 3 μl of 3M NaOAC and 75 μl of ethanol and placing the mixture on dry ice for 20 minutes. This solution was centrifuged to collect the DNA and the pellet briefly dried. The pellet was resuspended in 10 μl of annealing buffer, nucleotides (dG labeling mix), DTT, 35S-dATP, and sequenase 2.0 were added. The elongation reaction was run for 4 minutes before initiating the four 5 minute termination reactions with the ddNTP mixtures. The sequencing products were separated on an 8% acrylamide gel in TBE buffer and the sequence read from an overnight film exposure of the dried sequencing gel. Initial sequencing probes were the forward and reverse M13 sequencing primers from New England Biolabs which anneal to the vector on either side of the insert. As the sequence was determined, new primers were designed towards the end of the known sequence to continue through the gene.

The cDNA insert in pMON8581 (FIG. 3) had the largest insert that was identified by sequence analysis as a cDNA of a partial PAP gene. The clone in pMON8581 did not encode a protein large enough to be a full length clone so a new cDNA library was made using a kit from Invitrogen. cDNA was made starting with 3 μg of poly A+ selected RNA isolated from pokeweed leaves (as described above) in 40 μl of water. 12.5 μl of 0.1M MeHgOH (methyl mercuric hydroxide) was added and the mixture was incubated at room temperature for 7 minutes. Twenty-five (25) μl of water and 11 μl of 0.7 M β-mercaptoethanol were added and the mixture incubated for 5 minutes. The mixture was placed on ice and 1 μl of oligo dT, 2 μl of placental RNAase inhibitor, 50 μl of 5× reaction buffer, 5 μl of 25 mM dNTPs, 6 μl of reverse transcriptase and 125 μl water were added. The mixture was incubated at 42° C. for 90 minutes. The reaction was stopped by the addition of 10 μl 0.5M EDTA and 250 μl of phenol/chloroform. The aqueous layer was removed and 250 μl of 4M NH$_4$OAc and 1.0 ml of ethanol were added and the first strand of the cDNA precipitated on dry ice for 10 minutes and collected by centrifugation. The pellet was resuspended in 100 μl water, 100 μl of 4M NH$_4$OAc and 0.4 ml ethanol and the precipitation was repeated. The pellet was washed twice with 80% ethanol and then dried. The second strand of cDNA was synthesized by resuspending the pellet in 33 μl water and adding 5 μl of 10× second strand buffer, 2.5 μl 1.0 mg/ml BSA, 1 μl of 10 mM β-NAD+, 2 μl of 5.0 mM dNTPs, 4 μl RNAase H/E. coli DNA ligase and 2 μl DNA polymerase. The reaction was incubated at 15° C. for 60 minutes and at room temperature for an additional 60 minutes. The mixture was heated to 70° C. for 10 minutes, placed at room temperature for 2 minutes, and chilled on ice. T4 DNA polymerase (3.5 μl) was added and the reaction was incubated for 10 minutes at 37° C. The reaction was stopped by the addition of 2 μl of 0.5M EDTA and extracted with phenol/chloroform. The cDNA was precipitated from the aqueous phase by the addition of an equal volume of 4M ammonium acetate and three volumes of ethanol. The cDNA was collected by centrifugation.

BstXI non-palindromic linkers were ligated onto the ends of the cDNA by resuspending the pellet in 22 μl water and adding 3 μl of 10× ligation buffer, 3 μl of BstXI linkers and 2 μl of T4 DNA ligase. The mixture was incubated overnight at 15° C. The reaction was stopped by the addition of 2 μl of 0.5M EDTA and the DNA precipitated as described above. The cDNA was resuspended in TE and electrophoresed on a 1% agarose gel in TE buffer. A gel slice which contained cDNAs in the 500–1500bp range was cut out of the gel and the DNA was eluted for 2 hours at 150 volts using an electroeluter supplied by Invitrogen. The cDNA was precipitated and ligated into the BstXI cut pcDNAII vector from Invitrogen at 15° C. overnight. The ligation mix was transformed into E. coli DH1aF' cells and plated onto ten (10) 150 mm LB plates with 200 μg/ml ampicillin (LB amp plates) and incubated overnight at 37° C. When the colonies were 0.2 mm in diameter, the colonies were replicated onto duplicate nitrocellulose filters and incubated by overlaying fresh LB amp plates until colonies were transferred to Whatman 3MM paper saturated with 10% SDS for 3 minutes, then 0.5M NaOH for 5 minutes and finally to paper saturated with 0.5M sodium acetate for five minutes. The filters were then rinsed in 2×SSC, air dried for 30 minutes and baked at 80° C. for 2 hours. The baked filters were wetted in 2×SSC for 5 minutes and prewashed in 6×SSC, 0.5% SDS and 1 mM EDTA for 30 minutes at 50° C. Excess debris was removed with a chemwipe wetted in prewash solution. The filters were then treated overnight at 68° C. in a prehybridization solution of 6×SSC, 0.5% SDS, 100 μg/ml sheared salmon sperm DNA, 50 μg/ml tRNA and 5× Denhardt's solution using 10 ml for each filter. The prehybridization solution was poured off and replaced with hybridization solution; 6×SSC and 0.5% SDS, using 10 ml for each filter. The $^{32}$P labeled 600 bp EcoRI fragment from pMON8581 was added as a probe at 2×10$^6$ cpm/filter. The probe was labeled just prior to its use by random oligo priming. The labelled probe was purified on a G-25 spin column. Hybridization was performed for 14 hours at 68° C. and the filters were washed twice at 23° C. with 6×SSC, 0.2% SDS for 15 minutes and once at 68° C. and then exposed to film.

Figure 6:
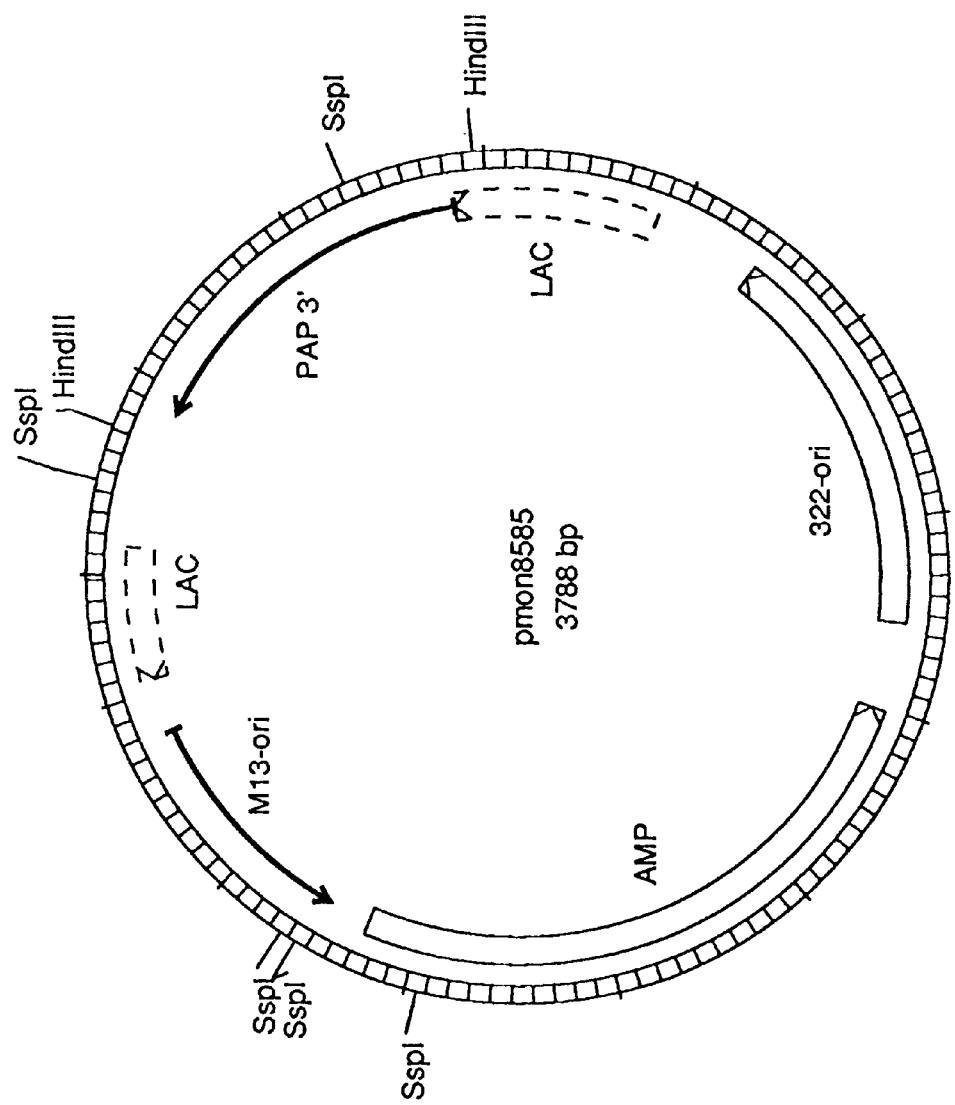
FIG. 6 shows the plasmid map of pMON8585.

Two positive colonies were identified. They were restreaked on LB amp plates and colonies patched onto duplicate LB-amp plates and the colony hybridization repeated to insure that the colony was pure. The inserts from two clones, pMON8585 and pMON8586 were completely sequenced as described above. The sequence of the cDNA insert in pMON8585 (FIG. 6) overlaps the cDNA insert in pMON8581 by several hundred base pairs at one end and has 15 adenines at the other, suggesting that the poly A portion of the RNA had been cloned. The inserts from pMON8581 and pMON8585 were spliced together to generate a full length cDNA by isolating the SalI to SspI fragment from pMON8581, the SspI to HindIII fragment from pMON8585 and ligating the two fragments into pUC119 that had been restricted with SalI and HindIII. The ligation mix was transformed into E. coli MC1061 and plated onto LB amp plates. Plasmid DNA from the resultant colonies was analyzed by restriction digestion for the presence of the two halves of the gene.

Figure 7:
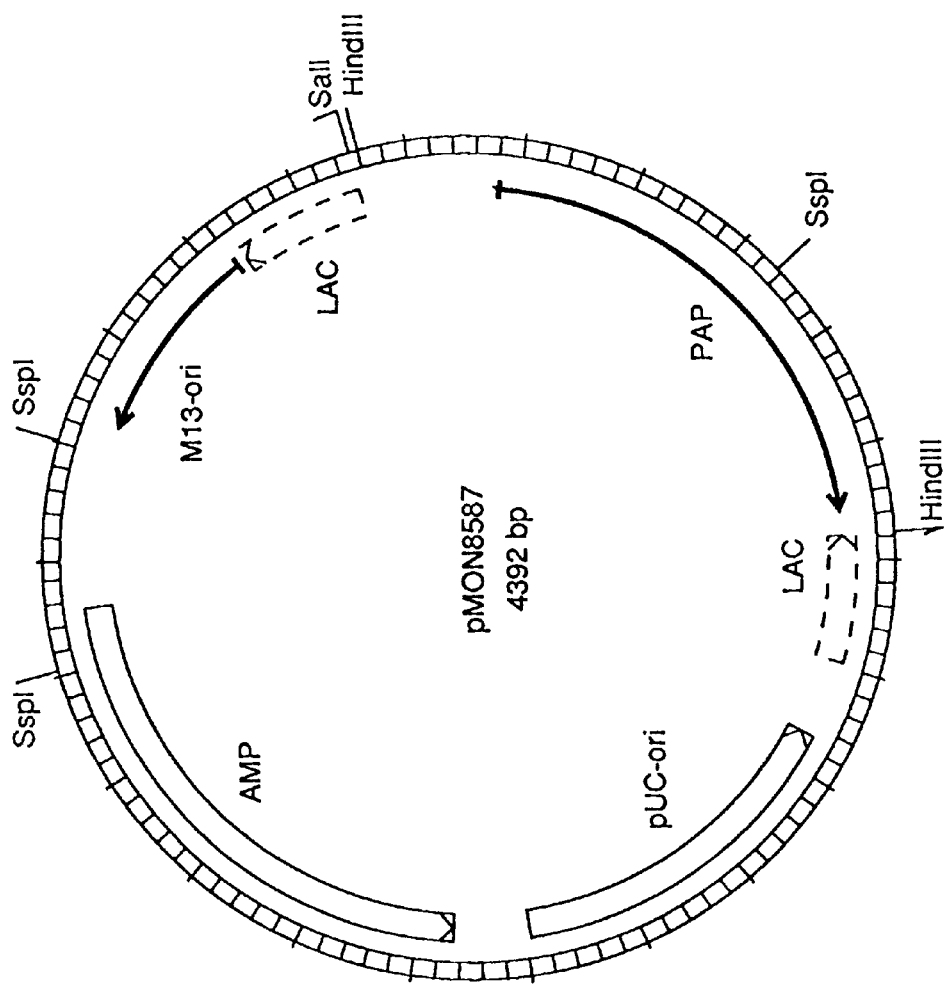
FIG. 7 shows the plasmid map of pMON8587.
Figure 8:
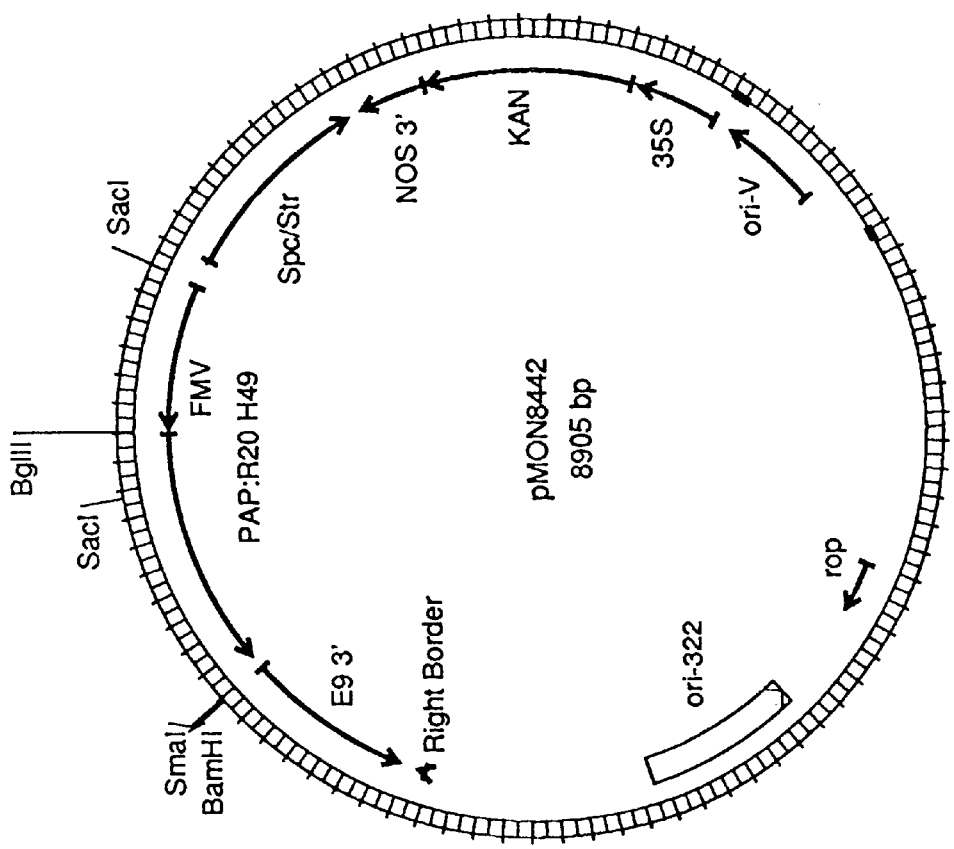
FIG. 8 shows a map of plasmid pMON8442.
Figure 9:
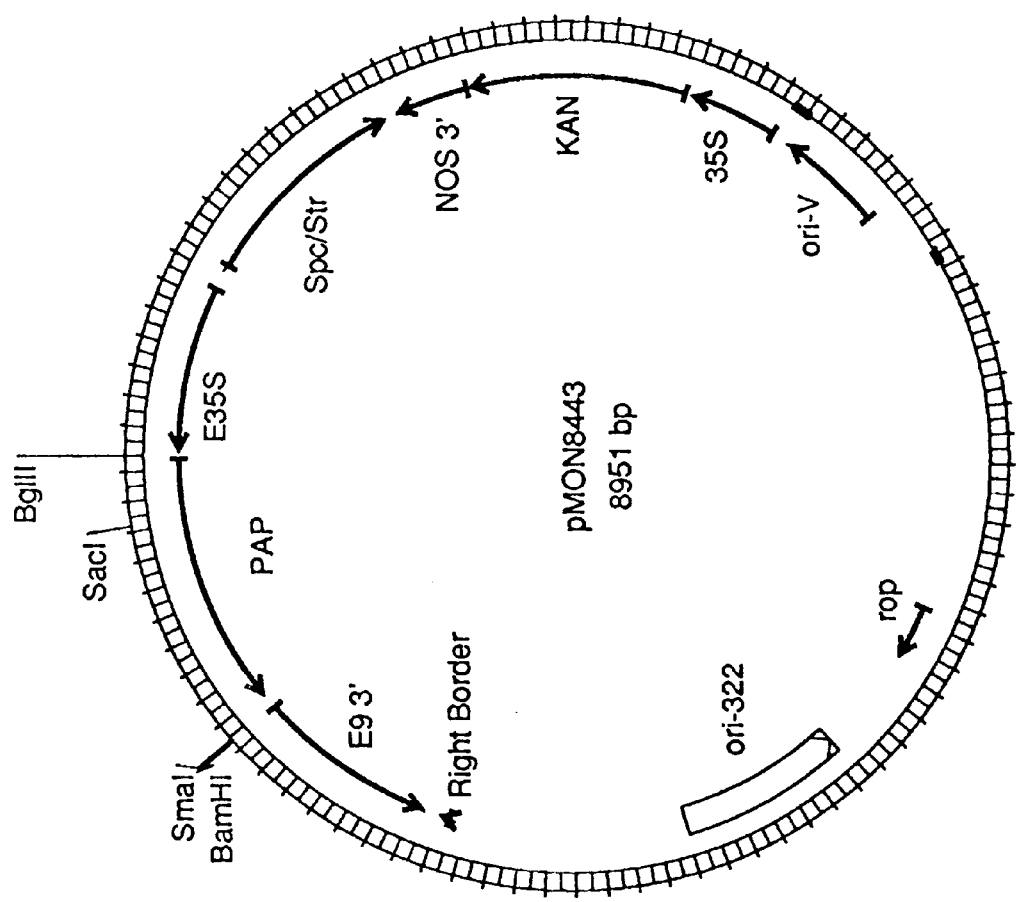
FIG. 9 shows a map of plasmid pMON8443.
Figure 10:
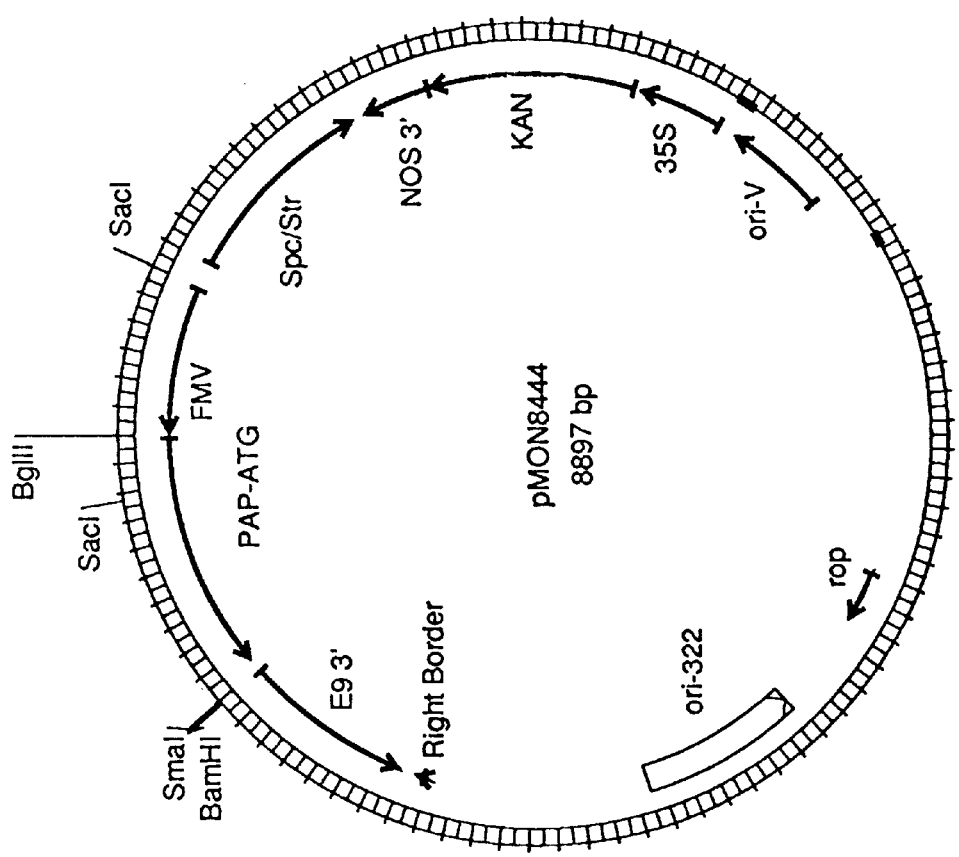
FIG. 10 shows a map of plasmid pMON8444.
Figure 11:
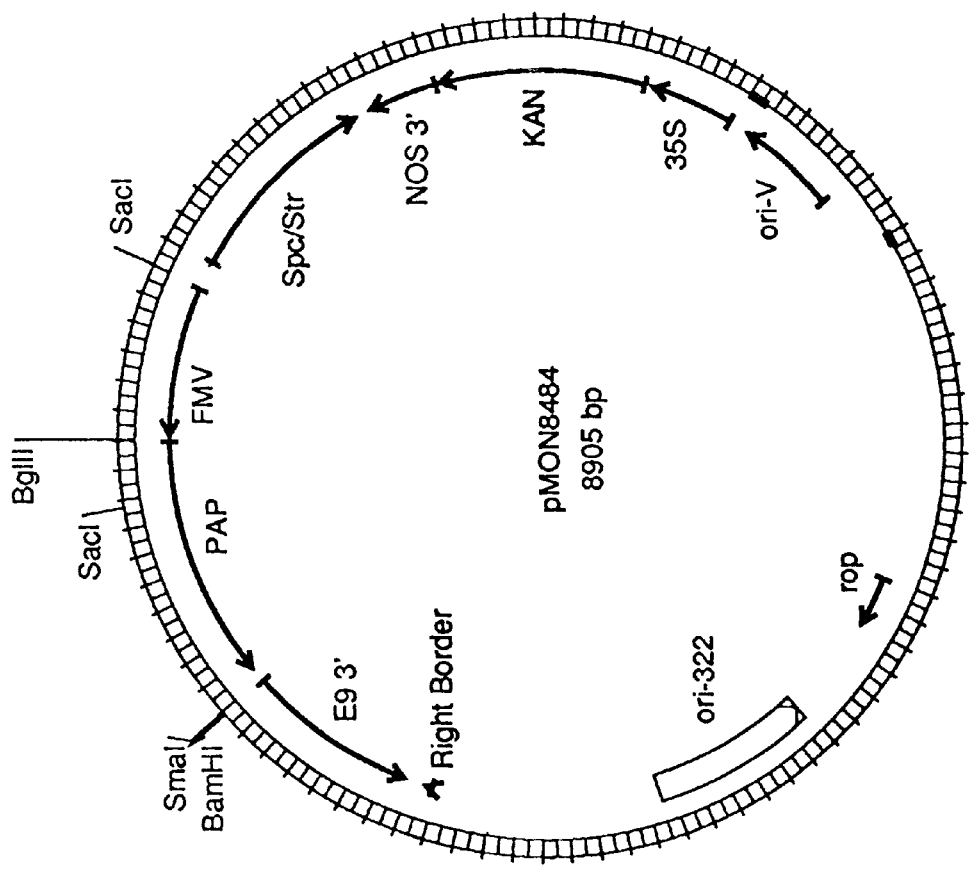
FIG. 11 shows a map of plasmid pMON8484.
Figure 12:
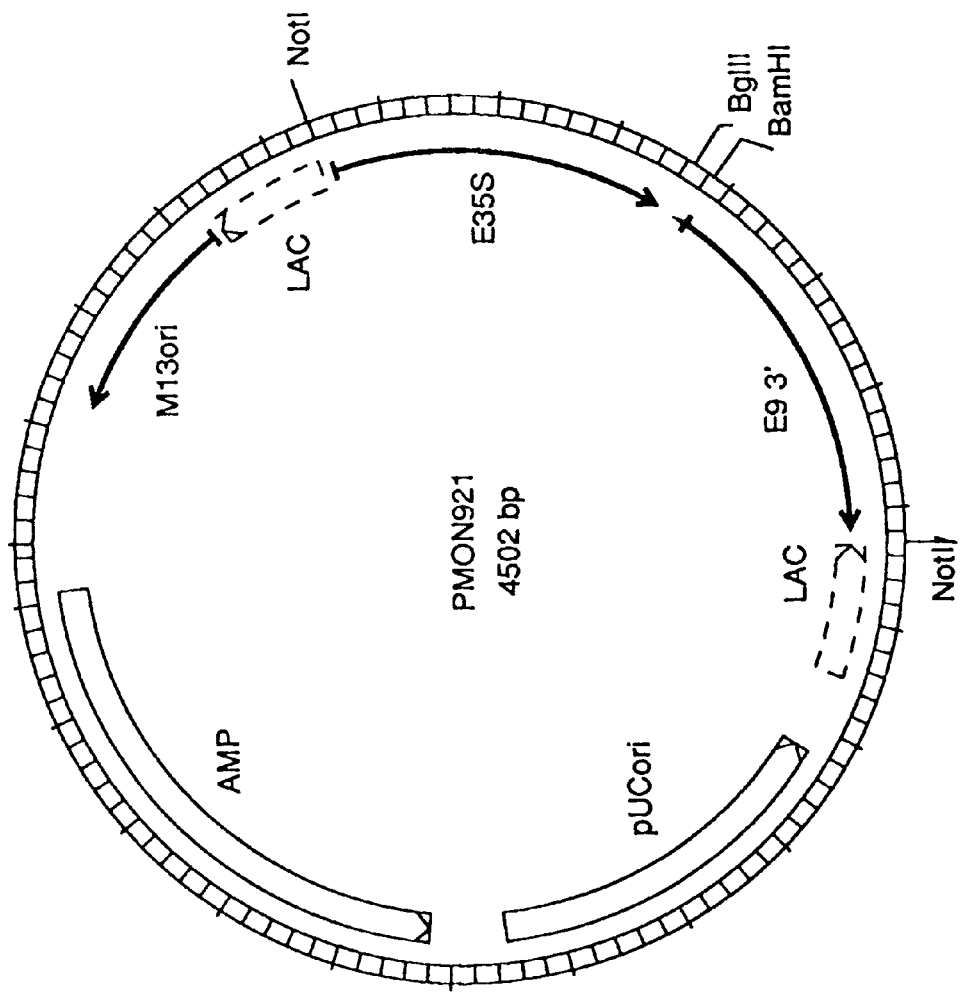
FIG. 12 shows a map of plasmid pMON921.
Figure 13:
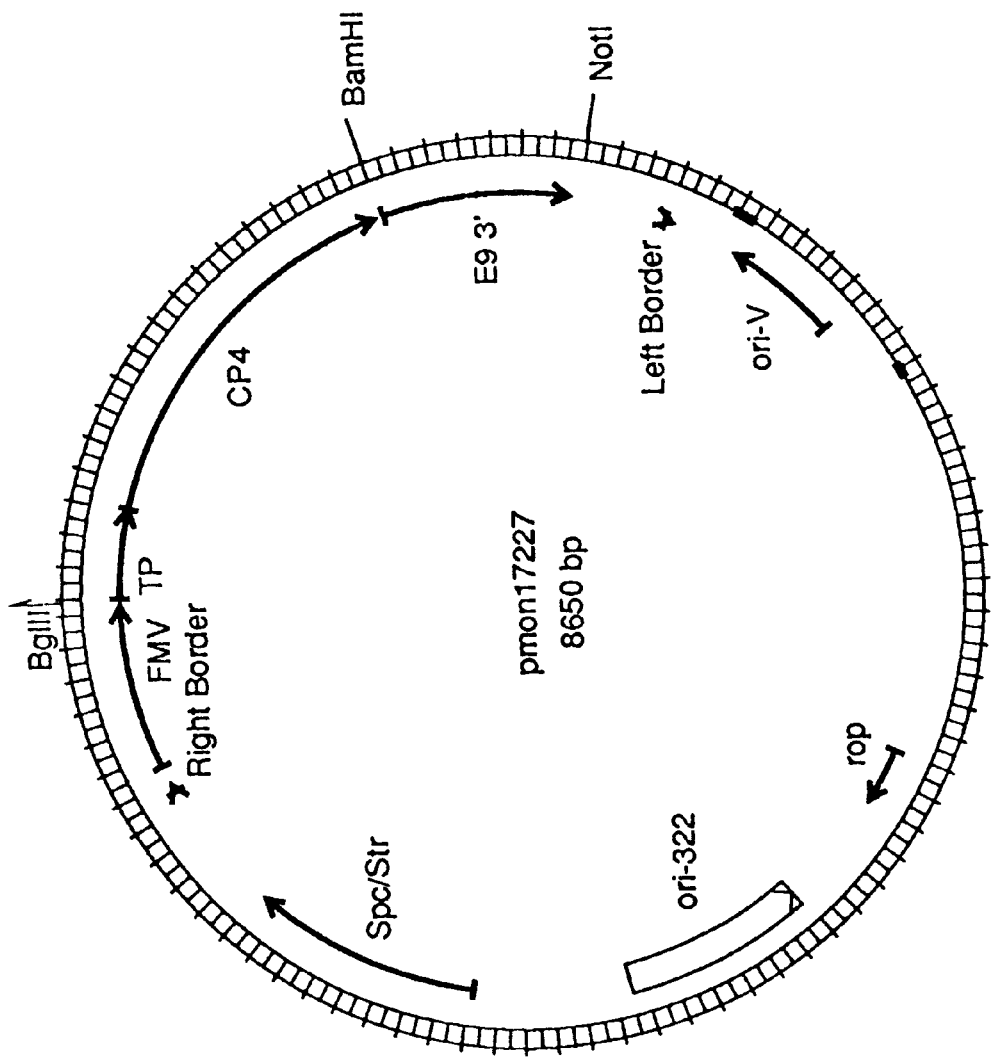
FIG. 13 shows a map of plasmid pMON17227.

FIG. 4 details the nucleotide sequence of the purified PAP'. There is a portion of the amino acid sequence that identically matches the previously determined 30 amino acids of the amino terminus of PAP beginning at amino acid 23 encoded by the cDNA, the valine residue. There are two methionine codons 19 and 22 codons 5' to the valine codon which could be possible translation start sites for a precursor protein. The presence of 19 to 22 extra amino acids at the N-terminus suggests a signal sequence to target the protein to the cell wall, where it is found in pokeweed leaves (Ready et al, 1986). Plasmid pMON8587 (FIG. 7) has the cDNA containing the entire coding sequence of the PAP gene cloned into pUC119.

The double stranded DNA sequence encoding PAP' or other form of pokeweed antiviral protein may be inserted into a suitable plant transformation vector for transformation into potato. Suitable plant transformation vectors include those derived from a Ti plasmid of *Agrobacterium tumefaciens*, as well as those disclosed, e.g. by Herrera-Estrella (1983), Bevan (1984), Klee (1985) and U.S. Pat. No. 4,940,838, issued to Schilperoort et al. A plant transformation vector preferably includes all of the necessary elements for transformation of plant cells. Typical plant cloning vectors comprise selectable and scoreable marker genes, T-DNA borders, cloning sites, appropriate bacterial genes to facilitate identification of transconjugates, broad host-range replication and mobilization functions and other elements as desired.

A structural DNA sequence encoding pokeweed antiviral protein is inserted into a plant transformation vector as a gene capable of being expressed in potato. A gene generally comprises, in sequence, a promoter which functions in plant cells, a 5' non-translated leader sequence, a structural DNA sequence coding for the desired protein, and a 3' non-translated region which functions in plants to cause the addition of polyadenylated nucleotides to the 3' end of the RNA sequence, each element being operably coupled to the adjacent element and in double stranded form. A plant gene comprising the above elements may be inserted by standard recombinant DNA methods into a plant transformation vector. Alternately, some or all of the elements of the plant gene may be present in the plant transformation vector and the remaining elements added to the vector when necessary. A plant transformation vector may be prepared that has all of the necessary elements for plant expression except the desired structural DNA sequence which can readily be added to the vector by known methods.

Figure 14:
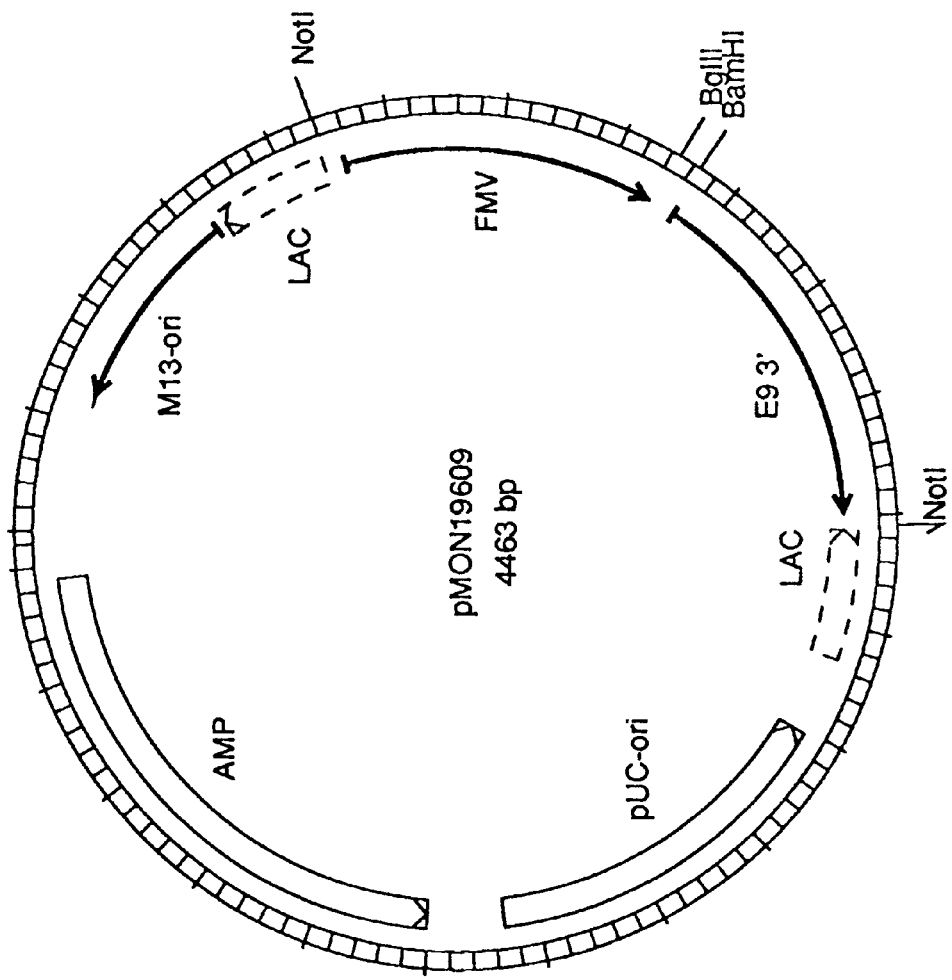
FIG. 14 shows a map of plasmid pMON19609.

Transcription of DNA into mRNA is regulated by a region of DNA referred to as the "promoter." The promoter region contains a sequence of bases that signals RNA polymerase to associate with the DNA strands as a template to make a corresponding complimentary strand of mRNA. A number of promoters which are known to cause transcription of DNA in plant cells can be used in this invention. Useful promoters may be obtained from a variety of sources such as plants or plant DNA viruses and include, but are not necessarily limited to, promoters isolated from the caulimovirus group such as the cauliflower mosaic virus 35S promoter (CaMV35S) and the figwort mosaic virus full-length transcript promoter (FMV35S). The DNA sequence of a useful FMV35S promoter is presented in FIG. 14 and is identified as SEQ ID NO:8. Other useful promoters include promoters which are capable of expressing pokeweed antiviral protein in an inducible or in a tissue specific manner in certain cell types where the virus infection is known to occur. For example, the promoters from phenylalanine ammonia lyase, chalcone synthase, hydroxyproline rich glycoprotein, extensin, pathogenesis related (PR) proteins and wound inducible protease inhibitor from potato would be useful because they are inducible promoters. Other promoters such as the promoter from glutamine synthetase for expression in vascular tissues or promoters from epidermal cells could be used to express the protein in certain cell types where virus infection can occur. The patatin promoter could be used to express the protein in the tuber. The particular promoter selected is preferably capable of causing sufficient expression to result in the production of an effective amount of pokeweed antiviral protein to prevent virus infection, but not such as to be detrimental to the potato cell. The promoters utilized in the double-stranded DNA molecules should be selected to confer expression in the tissues that viruses infect, including but not limited to the epidermal, vascular and mesophyll cells of the leaf.

The RNA produced by a DNA construct of the present invention also contains a 5' non-translated leader sequence. This sequence can be derived from the promoter selected to express the gene, and can be specifically modified so as to increase or decrease translation of the mRNA. The 5' non-translated region can also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be derived from an unrelated promoter or coding sequence as discussed above.

The 3' non-translated region of the chimeric plant gene contains a polyadenylation signal which functions in plants to cause the addition of adenylate nucleotides to the 3' end of the RNA. Examples of preferred 3' regions are (1) the 3' transcribed, non-translated regions containing the polyadenylate signal of Agrobacterium tumor-inducing (Ti) plasmid genes, such as the nopaline synthase (NOS) gene, and (2) plant genes like the soybean 7S storage protein genes and the pea small subunit of the ribulose-1,5-bisophosphate carboxylase (ssRUBISCO) E9 gene.

The DNA constructs of the present invention also contain a structural coding sequence, in double-stranded DNA form, which encodes an amino terminal signal sequence. This signal sequence localizes the pokeweed antiviral protein to the cell wall where it is physically separated from the plant ribosomes. This sequence can be derived from the pokeweed antiviral protein gene, but could be modified to increase translocation efficiency of the protein in a given plant species. Alternatively, the native signal sequence could be replaced with a heterologous signal sequence which translocates the pokeweed antiviral protein to the cell wall or extracellular compartments. Alternately, one could use an intracellular or organelle targeting signal sequence, such as a vacuolar targeting sequence, if desired.

In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen.

In particular, plant transformation vectors pMON977 and pMON981 were used as the basic plasmid to prepare a vector to be transformed into potato. These plasmids are made up of the following segments of DNA. The first is a 0.93 kb AvaI to engineered-EcoRV fragment isolated from transposon Tn7 that encodes bacterial spectinomycin/streptomycin resistance (Spc/Str), which is a determinant for selection in *E. coli* and *Agrobacterium tumefaciens*. This is joined to the 1.61 kb segment of DNA encoding a chimeric kanamycin resistance which permits selection of transformed plant cells. The chimeric gene (35S/KAN/NOS 3') consists of the cauliflower mosaic virus (CaMV) 35S promoter (Odell et al., 1985), the neomycin phosphotransferase type II (KAN or NPTII) gene, and the 3'-nontranslated region of the nopaline synthetase gene (NOS 3'). The next segment is the 0.75 kb ori containing the origin of replication from the RK2 plasmid (ori-V). It is joined to the 3.1 kb SalI to PvuI segment of pBR322 (ori-322) which provides the origin of replication for maintenance in *E. coli* and the bom site for the conjugational transfer into the *Agrobacterium tumefaciens* cells. The next segment is the 0.36 kb PvuI to BclI from pTiT37 which provides the right border for transfer of the tDNA. Then comes the 3'-nontranslated region of the small subunit RUBISCO gene (E9 3'). There is a polylinker between the E9 3' and the next segment which in pMON977 is the E35S promoter and in pMON981 is the FMV promoter. Genes such as one encoding pokeweed antiviral protein can be inserted into the polylinker so that their expression will be directed from the E35S promoter or the FMV promoter and will be polyadenylated using the signals on the E9 3' region.

The plant vectors were mobilized into the ABI Agrobacterium strain for transformation. The ABI strain is the A208 *Agrobacterium tumefaciens* carrying the disarmed Ti plasmid pTiC58 (pMP9RK) (Koncz and Schell, 1986). The Ti plasmid does not carry the T-DNA phytohormone genes and the strain is therefore unable to cause the crown gall disease. Mating of the plant vector into ABI was done by the triparental conjugation system using the helper plasmid pRK2013 (Ditta et al., 1980). When the plant tissue is incubated with the ABI::plant vector conjugate, the vector is transferred to the plant cells by the vir functions encoded by the disarmed pTiC58 plasmid. The vector opens at the T-DNA right border region, and the entire plant vector sequence may be inserted into the host plant chromosome. The pTiC58 Ti plasmid does not transfer to the plant cells but remains in the Agrobacterium.

Agrobacterium mediated transformation has proved to be particularly useful for the transformation of potato. A vector containing a pokeweed antiviral protein DNA sequence is first introduced into a disarmed Agrobacterium strain. Both single and double border transformation vectors may be delivered to the plant via the ABI strain. The single border vector opens at the T-DNA right border region and the entire vector sequence is inserted into the host plant chromosome. The right border is lost during transfer and integration. In a double border vector, the T-DNA segment between the right and left border region is transformed to the plant cell, therefore delivering only the chimeric genes of interest to the chromosome. The remainder of the vector and the border sequences are lost during transfer and integration.

Transformation of potato cells using an Agrobacterium mediated transformation protocol has been accomplished. Two protocols are described below, but those skilled in the art know that these protocols can be modified or optimized to fit particular needs. Agrobacterium containing the desired plant transformation vector is grown overnight in 2 mls of LBSCK broth. LBSCK contains 10 g NaCl, 5 g yeast extract, 10 g Bacto-Tryptone, 50 mg spectinomycin, 25 mg Chloramphenicol and 50 mg Kanamycin in a 1 liter volume, pH 7.0. The following day, the bacteria is diluted 1:10 with MSO or until an OD (optical density) reading of 0.2–0.3 is established. MSO contains 4.4 g MS salts (Sigma), 30 g sucrose and 2 ml $B_5$ vitamin (500×) in a 1 liter volume, pH 5.7. Leaves from the stem of potato plants that have been grown under sterile conditions for about three (3) weeks on PM media supplemented with 25 mg/l ascorbic acid are removed. PM media contains 4.4 g MS salts (Sigma), 30 g sucrose, 0.17 g $NaH_2PO_4H_2O$, 1 ml thiamine HCl and 0.1 g Inositol in a 1 liter volume, pH 6.0 and 0.2% Gelrite agar. The stems are placed on a vegetable slicer (~30–50 at a time) and cut into 3–5 mm segments. These stem explants are inoculated for 15 minutes with the diluted bacteria. Approximately 20 mls of bacterial solution is used per 1000 stem explants. The bacterial solution is removed by aspiration and the explants placed onto prepared co-culture plates. The co-culture plates contain ⅒ MSO with 1.5 mls of TxD cells overlayed with wetted filter paper. Approximately 50 explants are placed on each plate.

After a two (2) day co-culture period, explants are placed onto callus induction plates containing MSO plus 0.5 mg/l ZR (Zeatin riboside), 10 mg/l $AgNO_3$ and 0.1 mg/l NAA (naphthaleneacetic acid) for four (4) weeks. These plates also contain 100 mg/l kanamycin to select for transformed cells. After four (4) weeks, explants that exhibit growth in the presence of kanamycin are placed on shoot induction media which contains MSO plus 5.0 mg/l ZR, 10 mg/l $AgNO_3$ and 0.3 mg/l $GA_3$ (gibberellic acid) and 100 mg/l kanamycin for further selection. Shoots typically begin to appear at about six (6) weeks. The plants are then placed in sundae cups with PM media and allowed to grow for approximately 2 weeks. Plants are placed into soil, hardened off, and analyzed to verify transformation by assaying for the presence of a protein which confers resistance to the antibiotic kanamycin to the plant. If the plant is positive for expression of the protein, the plant is kept for further study and maintained in tissue culture.

Alternately, the explants may be placed on callus induction plates containing MSO plus 3.0 mg/l BA (6 Benzylaminopurine) and 0.01 mg/l NAA for four (4) weeks with 100 mg/l kanamycin for selection. For shoot induction, the explants are placed on MSO plus 0.3 mg/l $GA_3$ only and 100 mg/ml kanamycin for selection. Shoots begin to appear at about 8 weeks. Shoots are recallused on MSP-5 with 200 mg/ml kanamycin and assayed in two weeks. MSP-5 contains 4.4 g MS salts (Sigma), 5 ml SLLX vitamins (200×), 30 g sucrose, 2.25 ml BAP, 0.186 ml NAA in 1 liter, pH 5.6 and 0.2% Gelrite agar.

After the plant cells have been transformed and after transformed callus has been identified, the transformed callus tissue is regenerated into whole plants. Any known method for the regeneration of potato plants from callus can be used in connection with this invention or any other method for the regeneration of transformed potato tissue.

The transformation, expression and activity of pokeweed antiviral protein is described in the following exemplary embodiments. The following examples are provided to better elucidate the practice of the present invention and should not be interpreted in any way to limit the scope of the present invention. Those skilled in the art will recognize that various modifications can be made to the methods and genes described herein while not departing from the spirit and scope of the present invention.

EXAMPLE 1

Pokeweed antiviral protein was engineered for constitutive expression in plants to test if the gene was suitable for plant expression and if plants expressing this protein were resistant to viral infection.

In order to insert the PAP' gene (as previously described) into the plant expression vectors, the gene was modified to add a KpnI and BglII site at either of the possible start codons and a SmaI site at the 3' end of the gene. This was accomplished using PCR with pMON8587 (FIG. 7) as the template DNA and mutagenesis primers that had the desired restriction sites in their 5' end and matched the nucleotide sequence of the PAP' gene in their 3' end.

The mutagenesis PCR primers used were:

```
5'GGGGTACCAGATCTGAAGGGAAGATGAAGTCGATG (SEQ ID NO:5)

5'GGGGTACCAGATCTGACGAAGTCGATGCTTGTGG (SEQ ID NO:6)

5'GGGCCCGGGAAGCTTTATAATATAGTTGG (SEQ ID NO:7)
```

The primer identified as SEQ ID NO:5 (prepared by the Midland Company) anneals to the 5' end of the coding sequence and both possible translation start sites are included. The primer identified as SEQ ID NO:6 also anneals to the 5' end of the coding sequence, but causes the mutation of the first possible translation initiation codon of the PAP' gene and preserves the second. The primer identified as SEQ ID NO:7 (Midland Company) anneals to the 3' end of the gene, just after the end of the coding sequence. Two PCR reactions were done, one with SEQ ID NO:5 and SEQ ID NO:7 and a second with SEQ ID NO:6 and SEQ ID NO:7. The PCR ran for 25 cycles, consisting of a 1 minute at 94° C. denaturation step, 2 minutes at 50° C. for the annealing step and 3 minutes at 72° C. for the extension step. The resulting DNA was phenol extracted and ethanol precipitated. The fragments were restricted with BglII and SmaI, electrophoresed on a low melting agarose gel and the resulting 1000 bp fragment cut out of the gel. These fragments were ligated to pMON981 and pMON977 cut with BglII and SmaI, which positions the PAP gene to be expressed in plant cells from the FMV and E35S promoters, respectively. The PAP structural coding sequences derived from this PCR reaction were completely sequenced because PCR is known to induce mutations. One plasmid, pMON8442, had three changes in the gene sequence: a leucine at position 20 of the mature PAP' changed to an arginine; a tyrosine at position 49 of the mature PAP changed to a histidine and the third mutation had no effect on the amino acid encoded therein. Shown below are the primers used to make the gene fragments, the names of the plasmids and the promoter and the allele of the PAP' gene in the plasmids. The variant PAP' DNA sequence is referred to as PAP':$R_{20}$ $H_{49}$.

Primers SEQ ID NO:5 and SEQ ID NO:7.

pMON8442 (FMV PAP:$R_{20}$ $H_{49}$)
pMON8443 (E35S PAP)
pMON8484 (FMV PAP)
Primers SEQ ID NO:6 and SEQ ID NO:7.

pMON8444 (FMV PAP-ATG)

Plasmids pMON8442, pMON8443, pMON8444 and pMON8484 are shown in FIGS. 8–11, respectively, and were then mobilized into an ABI Agrobacterium strain for tobacco transformation. In pMON8444, the first translation initiation codon of the entire coding sequence was removed by mutagenesis leaving the second in-frame ATG codon intact.

For transformation of *N. tobacum*, young leaves from one-month old tobacco plants were covered with $dH_2O$ for 20–30 minutes to increase turgor pressure. The water was drained off, and the leaves covered with 10% chlorox for 15 minutes and then rinsed three times with sterile $dH_2O$. Squares of 0.5 cm were cut from the inside part of the leaf and placed on MS104 plates +2 ml 4COO5K to preculture for one day. A fresh overnight culture of Agrobacterium carrying the plant transformation vector was diluted 1:5 in 4COO5K media. The explants and Agrobacterium were mixed and then vortexed for 25 seconds. The liquid was drained off and the explants were blotted on sterile Whatman filter paper. The explants were transferred to selective plates containing kanamycin. They were incubated for several weeks until shoots formed, and were then transferred to rooting media. After roots formed, they were planted in soil. After at least one week of hardening off, the plants were sampled and tested for the presence of NPTII, by ELISA.

Transformation frequencies of *N. tobacum* cv Samsun and *N. benthemiana* typically range between 10 and 12% (number of transgenic plants obtained/leaf disk). The transformation frequencies for the different PAP plasmids are shown below.

| Plasmid | Species | % transformants |
|---|---|---|
| pMON8442 | N. benthemiana | 8.6% |
| pMON8442 | N. tobacum | 3.7% |
| pMON8443 | N. benthemiana | 1.0% |
| pMON8443 | N. tobacum | 0.7% |
| pMON8444 | N. tobacum | 0% |
| pMON8484 | N. tobacum | 0% |

Transformation frequencies for the PAP containing vectors was much lower than a typical transformation experiment. The transformation rates were highest for pMON8442, which expressed the mutated PAP:$R_{20}H_{49}$ gene. One possible explanation for the disparity in transformation frequencies between pMON8442 and pMON8484 is that the variant PAP is a less potent ribosome inhibitor. This possibility was tested by adding PAP or the variant PAP to an in vitro translation system. Transgenic tobacco plants which expressed either PAP' or the variant PAP' were ground in PBS to obtain a solution containing the sap of the plant. Various dilutions of the sap were added to a rabbit reticulocyte lysate containing $^{35}$S-methionine and either Brome Mosaic Virus or β-globin RNA. Sap from non-transgenic tobacco plants either spiked with PAP' or without added PAP' were also analyzed. TCA precipitable counts were measured by standard procedures. The data from these experiments exhibited no difference among the in vitro activity between the transgenic sap with PAP', transgenic sap with the variant PAP', and non-transgenic sap spiked with PAP'.

It is possible to modulate the level of PAP' expressed by several methods, including the use of different promoters, different 5' non-translated leaders, or different 3' non-translated regions. In addition, the signal sequence encoded in the PAP' gene, may not be the most efficient in a heterologous system, so fusing different signal sequences to the coding sequences for the mature protein may improve transformation efficiencies.

EXAMPLE 2

Transgenic *N.tobacum* and *N. benthemiana* plants were obtained which expressed the variant PAP' gene as assayed by ELISA. A #6 cork borer was used to sample the potential PAP expressing tobacco plants. Two 15–20 mg leaf disks were ground in 0.5 ml PBS-T (0.05% Tween). 200 μl of the ground plant extract and 50 μl of 1.0% ovalbumin were applied to a microtiter plate coated with a 1:2000 dilution of PAP' IgG, and incubated for four hours at 37° C. PAP standards of 10 ng, 3 ng, 1 ng, 0.3 ng, 0.1 ng and 0.03 ng were included on every plate, diluted into non-transgenic tobacco sap. The plate was washed several times with PBS-T and 250 μl of 1:5000 dilution PAP-IgG conjugated to alkaline phosphatase was added to each well and the plate incubated at 4° C. overnight. The conjugate was washed off the plate and substrate added. After color developed (usually 15–30 minutes) the plate was read at 405 nm. At least 30 *N. benthemiana* transformed with pMON8442 were obtained that had detectable levels of PAP', ranging between 0.1–10 ng of PAP/well, and at least eight similarly transformed *N. tobacum* contained detectable levels of PAP' within a similar range.

To test if the PAP':$R_{20}H_{49}$ protein has antiviral activity in vitro, plants were inoculated with virus in the presence of plant sap from highly expressing transgenic tobacco, vector control plant sap, or vector control plant sap plus PAP. The transgenic *N. benthemiana* plant, 29459, contained 2–10 ng of PAP/disk, and the transgenic *N. tobacum* plant, 29504, contained 1–3 ng of PAP/disk. Leaf disks were ground in 0.1M NaP buffer pH 7.0, 100 μl/disk and Potato virus X (PVX) was added to a final concentration of 1 μg/ml. PAP was added to a final concentration of 2 ng/50 μl to the vector control sap. Two leaves each of either *N. tobacum* cv Samsun (sam.) or *Chenopodium amaranthacolor* (chen.) were inoculated with 50 μl of plant sap-PVX mixture and lesions were counted 10 dpi. The results are shown in Table I. The transgenic sap containing PAP':$R_{20}H_{49}$ protected the plants from virus infection as well as control sap spiked with wild-type PAP', suggesting that the mutated protein retained antiviral activity.

TABLE I

| sap source | test plant | # of plants | Avg. # of lesions/leaf | Standard deviation |
|---|---|---|---|---|
| 29459 | chen. | 4 | 0.4 | 0.6 |
| vc + PAP | chen. | 4 | 0.8 | 1.2 |
| vc | chen. | 4 | 7.0 | 7.7 |
| 29504 | sam. | 5 | 0.4 | 0.6 |
| vc + PAP | sam. | 5 | 1.6 | 1.0 |
| vc | sam. | 5 | 5.6 | 5.6 |
| 29459 | chen. | 6 | 0.3 | 0.4 |
| vc + PAP | chen. | 6 | 0.9 | 1.0 |
| vc | chen. | 6 | 2.3 | 1.9 |

EXAMPLE 3

The variant form of PAP', PAP':$R_{20}H_{49}$, was expressed in vivo, to determine whether it was capable of protecting a transgenic plant from virus infection. Nine $R_0$ *N. benthemiana* plants which contained detectable levels of PAP':$R_{20}H_{49}$ (by ELISA) were inoculated with 50 μl of 1 μl/μg PVX. Six plants which were obtained in the transformation process but did not contain detectable PAP' were inoculated as controls. Expression of PAP is considered positive if between 0.2 ng and 10 ng of PAP per 10 mg of tissue was detected by ELISA. At 9 dpi, the inoculated leaves and the second systemic leaf above the inoculated leaves were harvested. The leaf tissue was ground in 10 volumes of PBS-T and 10 μl were loaded onto a coated microtiter plate in 240 μl of PBS-T. The plates were treated as described above. As shown in Table II, all of the controls contained high levels of PVX in the inoculated and systemic leaves. However, only 4 of the 9 PAP' expressors had detectable virus in either the inoculated or the systemic leaf at 9 dpi. At later timepoints, a young but fully expanded leaf was sampled and tested for the presence of PVX. At 42 dpi, one additional plant contained PVX in an upper leaf.

In a second experiment, three transgenic PAP':$R_{20}H_{49}$ expressing plants and eight non-transgenic wild-type *N. benthemiana* were inoculated with PVX. All of the wild-type plants became infected with PVX, but only one of the transgenic PAP':$R_{20}H_{49}$ expressing plants became infected. This data demonstrates that expression of a variant form of PAP' in planta can protect a transgenic plant from virus infection. Although expression of PAP' was necessary to provide resistance, the level of PAP detected by ELISA in the plants did not correlate with the level of resistance.

TABLE II

| plant # | Detection of PAP' by ELISA | Detection of PVX by ELISA | | | | |
|---|---|---|---|---|---|---|
| | | 9 dpi | | 13 dpi | 22 dpi | 42 dpi |
| | | inoc. | sys. | upper | upper | upper |
| Experiment 1 | | | | | | |
| 30236 | − | + | + | | | |
| 30238 | − | + | + | | | |
| 30246 | − | + | + | | | |
| 30247 | − | + | + | | | |
| 30250 | − | + | + | | | |
| 30255 | − | + | + | | | |
| 30277 | + | + | + | + | + | + |
| 30228 | + | − | − | − | − | − |
| 30229 | + | + | + | + | + | + |
| 30230 | + | − | − | − | − | − |
| 30231 | + | − | − | − | − | − |
| 30237 | + | − | − | − | − | + |
| 30245 | + | − | − | − | − | − |
| 30248 | + | + | − | + | + | + |
| 30249 | + | + | + | + | + | + |
| Experiment 2 | | | | | | |
| | | 9 dpi. | | 29 dpi | | |
| plant # | PAP' | inoc. | sys. | upper | | |
| 30223 | + | − | − | − | | |
| 30224 | + | + | − | + | | |
| 30244 | + | − | − | − | | |
| wt-1 | nd | + | + | + | | |
| wt-2 | nd | + | + | + | | |
| wt-3 | nd | + | + | + | | |
| wt-4 | nd | + | + | + | | |
| wt-5 | nd | + | + | + | | |
| wt-6 | nd | + | + | + | | |
| wt-7 | nd | + | + | + | | |
| wt-8 | nd | + | + | + | | | nd = not determined
+ = positive for PVX
− = negative for PVX

EXAMPLE 4

Tobacco plants, *N. tobacum* cv. Samsun, were transformed as described in Example 1 with pMON8443, which contains the wild type PAP' gene, and pMON8442, which contains the variant PAP gene PAP':$R_{20}H_{49}$. Transgenic plants that expressed PAP' or the variant PAP' were obtained. R1 progeny of self-fertilized transgenic plants were analyzed for expression of PAP' or the variant PAP' by ELISA and plants that contained detectable levels of PAP or variant PAP were challenged with 5 μg/μl PVY by mechanical inoculation. Ten plants from each line were challenged and analyzed by ELISA 17 dpi for the presence of PVY. As shown in Table III below, three different plant lines transformed with pMON8442 exhibited complete protection from infection by PVY. One plant line transformed with pMON8443, Samsun 33617, also exhibited complete protection, but the other line did not. Plants containing the pMON8442 construct that expressed high levels of PAP' showed stunting, mottling and grew slower than wild-type plants. Plants expressing the wild-type PAP' under the regulatory control of the enhanced CaMV35S promoter were indistinguishable from wild-type plants in appearance and growth patterns. The level of resistance did not always correlate with the level of expression of the PAP' or variant PAP' in the plant.

TABLE III

| Plant line | Percentage of Infected plants 17 dpi |
|---|---|
| Samsun 31635 (NPTII and PAP neg. control) | 100% (10/10) |
| Samsun 31636 (NPTII and PAP neg. control) | 90% (9/10) |
| Samsun 29472 (pMON8442) | 0% (0/10) |
| Samsun 29509 (pMON8442) | 0% (0/6) |
| Samsun 26139 (pMON8442) | 0% (0/20) |
| Samsun 33617 (pMON8443) | 0% (0/10) |
| Samsun 31614 (pMON8443) | 100% (10/10) |

EXAMPLE 5

R1 progeny of several transgenic tobacco lines expressing PAP' or variant PAP' were tested for resistance to PVY by inoculation with viruliferous aphids. Five aphids were used to inoculate each plant and plants were analyzed by ELISA 12 days post inoculation. Results of this experiment, summarized in Table IV, show that transgenic lines 26139 and 29472, containing pMON8442, are resistant to aphid transmission of PVY. These lines were also resistant to mechanical transmission of PVY. Transgenic lines 29491 and 29509 containing pMON8442 did not show any resistance to aphid transmission of PVY. Line 29509 was resistant to mechanical transmission of PVY and line 29491 was not otherwise tested. Transgenic line 33617, containing pMON8443, was resistant to aphid transmission of PVY as well as resistant to mechanical transmission of PVY.

TABLE IV

| Plant Line | Percentage of Infected Plants |
|---|---|
| Samsun | 60% (9/15) |
| 26139 (pMON8442) | 6% (1/17) |
| 29472 (pMON8442) | 16% (1/6) |
| 29509 (pMON8442) | 100% (3/3) |
| 29491 (pMON8442) | 57% (8/14) |
| 33617 (pMON8443) | 22% (2/9) |

EXAMPLE 6

A transgenic potato line, identified as line 555, containing pMON8442 was obtained which expressed the variant PAP'. The transgenic potato plant was obtained using the transformation protocol as previously described. Plants from this line were propagated and challenged with PVX, PVY and PLRV. As shown in Table V, plants from this line exhibited resistance to PVX and PVY, but resistance to PLRV was not identified. In PVX experiments, seven plants propagated as cuttings from each line were inoculated with 5 $\mu$g/ml PVX and assayed by ELISA at 18 dpi and 22 dpi. PVY experiments were conducted similarly except that the plants were inoculated with 20 $\mu$g/ml PVY. For the PLRV experiment, fourteen plants from line 555 and 12 nontransformed potato plants (RBID) were inoculated with PLRV using viruliferous aphids. Each plant was assayed by ELISA 32 dpi.

TABLE V

| | Percentage of Plants showing PVX | |
|---|---|---|
| Plant | 18 dpi | 27 dpi |
| Line 555 | 0% | 14% |
| RBID | 100% | 85% |
| | Percentage of Plants showing PVY | |
| Plant | 19 dpi | 27 dpi |
| Line 555 | 14% | 14% |
| RBID | 85% | 85% |
| | Percentage of Plants showing PLRV | |
| Plant | 32 dpi | |
| Line 555 | 100% | |
| RBID | 100% | |

Even though potato line 555 did not exhibit resistance to PLRV, it is expected that when additional potato lines expressing the variant PAP' or another pokeweed antiviral protein are obtained, such plants will exhibit resistance to PLRV. This expectation is supported by the data presented in Example 5 where transgenic tobacco lines expressing PAP' provided resistance to infection by PVY transmitted by aphids, since PLRV is also transmitted by aphids.

EXAMPLE7

In order to determine whether PAP' or the variant PAP' is capable of conferring resistance to PLRV, three new plant transformation vectors were constructed. The cDNA sequence for PAP' was excised as a BglII-BamHI restriction fragment from pMON8443 and cloned into pMON921, a map of which is presented in FIG. 12, which had been digested with BglII and BamHI. In pMON921, the expression of the PAP' is driven by the enhanced CaMV35S promoter (E35S). Downstream of the PAP' coding sequence is the 3' nontranslated region of the small subunit gene from ribulose 1,5-bisphosphate carboxylase (E9 3'). Plasmid pMON921 also contains the M13 origin of replication (M13ori), the ampicillin resistance gene (AMP), the pUC origin of replication (pUCori), and a gene encoding beta galactosidase (LAC), which is interrupted by the E35S promoter and the E9 3' end. In similar fashion, the cDNA sequence for the variant PAP was excised from pMON8442 with BglII and BamHI and cloned into pMON921.

A NotI fragment containing the E35S promoter, the PAP' or variant PAP' cDNA coding sequence, and the E9 3' end was excised from pMON921 and cloned into the NotI site of the plant transformation vector pMON17227, a map of which is presented in FIG. 13. pMON17227 is made up of the following segments of DNA: the bacterial spectinomycin/streptomycin resistance gene (Spc/Str), followed by the right border of the tDNA. Adjacent to the right border is the synthetic bacterial CP4 EPSPS gene driven by the FMV35S promoter (see PCT publication WO92/04449). The CP4 gene confers the capability of using glyphosate as the means for selecting transformants. A chloroplast transit peptide from the Arabidopsis EPSP synthase is fused to the CP4 gene to target this gene to the chloroplasts. At the 3' end of the CP4 gene is the E9 3' end. This is followed by the left border of the tDNA, the origin of replication from the RK2 plasmid (ori-V) and the pBR322 origin of replication (ori-322) as described for vectors pMON977 and pMON981.

Another plant expression vector was constructed, in which the BglII-BamHI fragment containing the PAP'-variant sequence was excised from pMON8442 and cloned into pMON1909, which had been digested with BglII and BamHI. A map of pMON1909 is presented in FIG. 14. In pMON1909, the expression of PAP' variant is driven by the FMV promoter. Downstream of the PAP' variant sequence is the E9 3' end. Plasmid pMON1909 also contains the M13 origin of replication (M13-ori), the ampicillin resistance gene (AMP), the pUC origin of replication (pUC-ori), and beta-galactosidase gene, which is interrupted by the FMV promoter and E9 3' end.

A Not1 fragment containing the FMV promoter, the coding sequence of the PAP' variant and E9 3' end, was excised from pMON1909 and cloned into the Not1 site of the plant transformation vector, pMON17227.

The pMON17227 plant vectors containing either PAP' or a variant PAP' can then be mobilized into an ABI Agrobacterium strain for transformation of potato plants as previously described. To transform potatoes using glyphosate as a selectable marker, the Agrobacterium containing the desired vector is grown overnight in 2ml of LBSCK media. The following day, the bacteria is diluted 1:10 with MSO or until an optical density reading of about 0.2–0.3 is established. Potato plants are grown under sterile conditions for about 3 weeks on PM media supplemented with 25 mg/l ascorbic acid and then the leaves are removed. The remaining stem is cut into 3–5mm segments and inoculated with the diluted bacteria.

Explants are then placed onto prepared coculture plates containing ⅒ MSO with 1.5 mls of TxD cells overlayed with wetted filter paper. About 50 explants are placed on each plate. The explants are allowed to coculture for two days and are then placed onto callus induction media containing 5.0 mg/l Zeatin Riboside, 10 mg/l AgNO$_3$ and 0.1 mg/l NAA for 2 days. The explants are subsequently transferred onto callus induction media as described above including 0.025 mM glyphosate for selection. After about 4 weeks, explants are then placed onto shoot induction media which contains 5.0 mg/l Zeatin Riboside, 10 mg/l AgNO$_3$ and 0.3 mg/l GA3, with 0.025 mM glyphosate for selection. Shoots should begin to appear at about 8 weeks. The explants are then transferred to fresh shoot induction media every 4 weeks for 12 weeks. Shoots are excised and placed on PM media for about 2 weeks or until they are large enough to be planted in soil.

The resulting potato plants are then assayed for the expression of PAP' or variant PAP' by ELISA or immunoblot analysis. Potato plants that express either the PAP' or the variant PAP and nontransformed control potato plants will then be propagated by cuttings and inoculated with PLRV using 10–20 viruliferous aphids. Leaf samples will be obtained at 4, 5, and 6 weeks post inoculation and assayed for the presence of PLRV by ELISA. It is expected that some of the transgenic potato lines generated by this method will exhibit resistance to infection by PLRV.

EXAMPLE 8

To test whether PAP' had insecticidal properties, purified PAP' was painted onto tomato leaves at various concentrations. PAP' was diluted to the appropriate concentration in saline buffer and painted onto three tomato leaves. The leaves were allowed to dry and placed into three separate petri dishes. Five larva/dish were added. The leaves were placed in small petri dishes, and 5 first instar larvae of either Colorado potato beetle (a coleopteran) or Tobacco hornworm (a lepidopteran) were added. The insects were allowed to feed for three days, and then the number of live insects were counted and the damage to the leaf tissue was assessed. As shown in Table VI, PAP' was effective as an insecticide against the Colorado potato beetle at the lowest concentration tested, 20 μg/ml, and against the tobacco hornworm at 50 μg/ml whereas the buffer control had no effect. Percent survival is the percent (out of 15) of the larva that were still alive after three days. The damage to the leaves were assessed after 3 days using the following scale: 0=no damage, 1=slight, 2=moderate, 3=severe, and nl=no leaf left.

TABLE VI

| PAP' | Colorado potato beetle | | Tobacco Hornworm | |
|---|---|---|---|---|
| concentration | % survival | leaf damage | % survival | leaf damage |
| 270 μg/ml | 0 | 0 | 0 | 0 |
| 100 μg/ml | 0 | 0 | 0 | 0 |
| 50 μg/ml | 7 | 0 | 53 | 1 |
| 20 μg/ml | 20 | 1 | 73 | 3 |
| buffer only | 100 | nl | 100 | nl |

EXAMPLE 9

Three transgenic *N. tobacum* plants and three transgenic *N. benthemiana* plants expressing PAP':$R_{20}H_{49}$ were tested in a feeding assay using Tobacco hornworms similar to these described above in Example 8. Plants transformed with pMON977, which does not contain a PAP' gene (vc), were used as a control. The results are shown in Table VII. One transgenic plant, 29489, was lethal to the hornworms and this result was confirmed on repetition of the experiment. The transgenic plants were assayed for PAP' by ELISA as described above and by western. Percent survival is the percent of larvae, out of 5, that survived after three days of feeding on the transgenic plant tissue.

TABLE VII

| Plant # | species[1] | PAP' by ELISA | PAP' by western | % survival |
|---|---|---|---|---|
| vc | b | − | − | 100 |
| 29459 | b | + | | 100 |
| 29462 | b | + | | 100 |
| 29467 | b | + | | 100 |
| vc | t | − | − | 100 |
| 29489 | t | + | + | 0 |
| 29504 | t | + | | 100 |
| 29510 | t | + | | 100 |

[1]b = *N. benthemiana*, t = *N. tobacum*

From the foregoing, it will be seen that this invention is one well adapted to attain all the ends and objects hereinabove set forth together with advantages which are obvious and which are inherent to the invention. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying figures is to be interpreted as illustrative and not in a limiting sense.

BIBLIOGRAPHY

Beachy, R., S. Loesch-Fries and N. Tumer (1990) *Ann. Rev. Phytopathology.*

Bevan, M. (1984) *Nucl.Acids Res.* 12: 8711–8721.

Bjorn, M. J. et al. (1984) *Biochimica et Biophysica Acta*, 790 pp. 154–163.

Coruzzi, G., R. Broglie, C. Edwards and N. H. Chua (1984) *Embo* 3: 1671–1679

Herrera-Estrella, L. et al. (1983) *Nature* 303: 209.

Houston, L. L. et al. (1983) *The Journal of Biological Chemistry*, Vol. 258, No. 16, Issue of August 25, pp. 9601–9604.

Irvin, J. D., T. Kelley and J. D. Robertus (1980) *Arch. of Biochem. and Biophys.*, Vol. 200, No. 2, pp. 418–425.

Klee, H. J. et al. (1985) *Bio/Technology* 3: 637–42.

Klinkowski, M., Pflanzliche Virologie, Registerband (1977) *Akademie-Verliag-Berlin*, p.145.

Koncz, C. and J. Schell (1986) *Mol. Gen. Genet.* 201: 383–396.

Odell, J. T., F. Nagy and N. H. Chua (1985) *Nature* 313: 810–812.

Ready, M. P., D. T. Brown and J. D. Robertus (1986) *Proc. Natl. Acad. Sci.* USA Vol. 83, pp 5053–5056.

Schonfelder, M. et al. (1990) VIIIth International Congress of Virology Abstracts, number P81-013.

Tomlinson, J. A., V. M. Walker, T. H. Flewett and G. R. Barclay (1974) *Journal of Gen. Virol.* No. 22, pp. 225–232.

Wyatt, S. D. and R. J. Shepherd (1969) *Phytopathology*, Vol. 59, pp. 1787–1794.

What is claimed is:

1. A potato plant comprising a heterologous gene capable of causing the expression of a pokeweed antiviral protein in said plant at a level sufficient to render said plant resistant to infection by a virus selected from the group consisting of potato virus X and potato virus Y.

2. A potato plant according to claim 1 wherein said heterologous gene comprises:

a promoter that functions in plant cells to cause the production of an RNA sequence; which is operably linked to a structural DNA sequence which causes the production of an RNA encoding a fusion protein comprising an N-terminal signal sequence and a pokeweed antiviral protein, said signal sequence capable of causing the translocation of said pokeweed antiviral protein to the cell wall of said plant; which is operably linked to a 3' non-translated region that functions in plant cells to cause the addition of polyadenylate nucleotides to the 3' end of said RNA sequence.

3. A potato plant according to claim 2 wherein said promoter is capable of tissue specific expression of said pokeweed antiviral protein in at least one of the epidermal, vascular or mesophyll cells of said plant.

4. A potato plant according to claim 2 wherein said promoter is selected from the group consisting of the FMV35S promoter and the CaMV 35S promoter.

5. A potato plant according to claim 2 wherein said promoter is an inducible promoter.

6. A potato plant according to claim 2 wherein said structural DNA sequence is SEQ ID NO:1.

7. A potato plant according to claim 2 wherein said structural DNA sequence is SEQ ID NO:2.

8. A potato plant comprising a heterologous gene capable of causing the expression of a pokeweed antiviral protein and the translocation of said protein to the cell walls or vacuoles of said plant, said protein expressed at a level sufficient to render said plant resistant to infection by a virus selected from the group consisting of potato virus X and potato virus Y.

9. A potato tuber comprising a heterologous gene capable of causing the expression of a pokeweed antiviral protein in said tuber at a level sufficient to render said tuber resistant to infection by a virus selected from the group consisting of potato virus X and potato virus Y.

10. A potato tuber according to claim 9 wherein said heterologous gene comprises:

a promoter that functions in plant cells to cause the production of an RNA sequence; which is operably linked to a structural DNA sequence which causes the production of an RNA encoding a fusion protein comprising an N-terminal signal sequence and a pokeweed antiviral protein, said signal sequence capable of causing the translocation of said pokeweed antiviral protein to the cell wall of said plant; which is operably linked to a 3' non-translated region that functions in plant cells to cause the addition of polyadenylate nucleotides to the 3' end of said RNA sequence.

11. A potato tuber according to claim 10 wherein said promoter is capable of tissue specific expression of said pokeweed antiviral protein in said tuber.

12. A potato tuber according to claim 10 wherein said promoter is selected from the group consisting of the FMV35S promoter and the CaMV 35S promoter.

13. A potato tuber according to claim 10 wherein said promoter is an inducible promoter.

14. A potato tuber according to claim 10 wherein said structural DNA sequence is SEQ ID NO:1.

15. A potato tuber according to claim 10 wherein said structural DNA sequence is SEQ ID NO:2.

16. An isolated DNA sequence comprising SEQ ID NO:2.

17. A method for providing viral resistance to infection by a virus selected from the group consisting of potato virus X and potato virus Y in a potato plant or tuber comprising causing the expression of a pokeweed antiviral protein in said plant or tuber.

18. The method of claim 17 wherein said potato plant or tuber is transformed with a heterologous gene comprising:

a promoter that functions in plant cells to cause the production of an RNA sequence; which is operably linked to a structural DNA sequence which causes the production of an RNA encoding a fusion protein comprising an N-terminal signal sequence and a pokeweed antiviral protein, said signal sequence capable of causing the translocation of said pokeweed antiviral protein to the cell wall of said plant; which is operably linked to a 3' non-translated region that functions in plant cells to cause the addition of polyadenylate nucleotides to the 3' end of said RNA sequence.

19. The method of claim 17 wherein said structural DNA sequence is SEQ ID NO:1.

20. The method of claim 17 wherein said structural DNA sequence is SEQ ID NO:2.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 1379 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:1:

```
CTATGAAGTC GGGTCAAAGC ATATACAGGC TATGCATTGT TAGAAACATT GATGCCTCTG      60
ATCCCGATAA ACAATACAAA TTAGACAATA AGATGACATA CAAGTACCTA AACTGTGTAT     120
GGGGGAGTGA AACCTCAGCT GCTAAAAAAA CGTTGTAAGA AAAAAGAAA GTTGTGAGTT     180
AACTACAGGG CGAAAGTATT GGAACTAGCT AGTAGGAAGG GAAGATGAAG TCGATGCTTG     240
TGGTGACAAT ATCAATATGG CTCATTCTTG CACCAACTTC AACTTGGGCT GTGAATACAA     300
TCATCTACAA TGTTGGAAGT ACCACCATTA GCAAATACGC CACTTTTCTG AATGATCTTC     360
GTAATGAAGC GAAAGATCCA AGTTTAAAAT GCTATGGAAT ACCAATGCTG CCCAATACAA     420
ATACAAATCC AAAGTACGTG TTGGTTGAGC TCCAAGGTTC AAATAAAAAA ACCATCACAC     480
TAATGCTGAG ACGAAACAAT TTGTATGTGA TGGGTTATTC TGATCCCTTT GAAACCAATA     540
AATGTCGTTA CCATATCTTT AATGATATCT CAGGTACTGA ACGCCAAGAT GTAGAGACTA     600
CTCTTTGCCC AAATGCCAAT TCTCGTGTTA GTAAAAACAT AAACTTTGAT AGTCGATATC     660
CAACATTGGA ATCAAAAGCG GGAGTAAAAT CAAGAAGTCA GGTCCAACTG GAATTCAAA     720
TACTCGACAG TAATATTGGA AAGATTTCTG GAGTGATGTC ATTCACTGAG AAAACCGAAG     780
CCGAATTCCT ATTGGTAGCC ATACAAATGG TATCAGAGGC AGCAAGATTC AAGTACATAG     840
AGAATCAGGT GAAAACTAAT TTTAACAGAG CATTCAACCC TAATCCCAAA GTACTTAATT     900
TGCAAGAGAC ATGGGGTAAG ATTTCAACAG CAATTCATGA TGCCAAGAAT GGAGTTTTAC     960
CCAAACCTCT CGAGCTAGTG GATGCCAGTG GTGCCAAGTG GATAGTGTTG AGAGTGGATG    1020
AAATCAAGCC TGATGTAGCA CTCTTAAACT ACGTTGGTGG GAGCTGTCAG ACAACTTATA    1080
ACCAAAATGC CATGTTTCCT CAACTTATAA TGTCTACTTA TTATAATTAC ATGGTTAATC    1140
TTGGTGATCT ATTTGAAGGA TTCTGATCAT AAACATAATA AGGAGTATAT ATATATTACT    1200
CCAACTATAT TATAAAGCTT AAATAAGAGG CCGTGTTAAT TAGTACTTGT TGCCTTTTGC    1260
TTTATGGTGT TGTTTATTAT GCCTTGTATG CTTGTAATAT TATCTAGAGA ACAAGATGTA    1320
CTGTGTAATA GTCTTGTTTG AAATAAAACT TCCAATTATG ATGCAAAAAA AAAAAAAA     1379
```

(2) INFORMATION FOR SEQ ID NO:2:

(i) SEQUENCE CHARACTERISTICS:
       (A) LENGTH: 1379 base pairs
       (B) TYPE: nucleic acid
       (C) STRANDEDNESS: single
       (D) TOPOLOGY: linear (ii) MOLECULE TYPE: cDNA (xi) SEQUENCE DESCRIPTION: SEQ ID NO:2:

```
CTATGAAGTC GGGTCAAAGC ATATACAGGC TATGCATTGT TAGAAACATT GATGCCTCTG      60
```

-continued

```
ATCCCGATAA ACAATACAAA TTAGACAATA AGATGACATA CAAGTACCTA AACTGTGTAT      120

GGGGGAGTGA AACCTCAGCT GCTAAAAAAA CGTTGTAAGA AAAAAAGAAA GTTGTGAGTT      180

AACTACAGGG CGAAAGTATT GGAACTAGCT AGTAGGAAGG GAAGATGAAG TCAATGCTTG      240

TGGTGACAAT ATCAATATGG CTCATTCTTG CACCAACTTC AACTTGGGCT GTGAATACAA      300

TCATCTACAA TGTTGGAAGT ACCACCATTA GCAAATACGC CACTTTTCGG AATGATCTTC      360

GTAATGAAGC GAAAGATCCA AGTTTAAAAT GCTATGGAAT ACCAATGCTG CCCAATACAA      420

ATACAAATCC AAAGCACGTG TTGGTTGAGC TCCAAGGTTC AAATAAAAAA ACCATCACAC      480

TAATGCTGAG ACGAAACAAT TTGTATGTGA TGGGTTATTC TGATCCCTTT GAAACCAATA      540

AATGTCGTTA CCATATCTTT AATGATATCT CAGGTACTGA ACGCCAAGAT GTAGAGACTA      600

CTCTTTGCCC AAATGCCAAT TCTCGTGTTA GTAAAAACAT AAACTTTGAT AGTCGATATC      660

CAACATTGGA ATCAAAAGCG GGAGTAAAAT CAAGAAGTCA GGTCCAACTG GAATTCAAA       720

TACTCGACAG TAATATTGGA AAGATTTCTG GAGTGATGTC ATTCACTGAG AAAACCGAAG      780

CCGAATTCCT ATTGGTAGCC ATACAAATGG TATCAGAGGC AGCAAGATTC AAGTACATAG      840

AGAATCAGGT GAAAACTAAT TTTAACAGAG CATTCAACCC TAATCCCAAA GTACTTAATT      900

TGCAAGAGAC ATGGGGTAAG ATTTCAACAG CAATTCATGA TGCCAAGAAT GGAGTTTTAC      960

CCAAACCTCT CGAGCTAGTG GATGCCAGTG GTGCCAAGTG GATAGTGTTG AGAGTGGATG     1020

AAATCAAGCC TGATGTAGCA CTCTTAAACT ACGTTGGTGG GAGCTGTCAG ACAACTTATA     1080

ACCAAAATGC CATGTTTCCT CAACTTATAA TGTCTACTTA TTATAATTAC ATGGTTAATC     1140

TTGGTGATCT ATTTGAAGGA TTCTGATCAT AAACATAATA AGGAGTATAT ATATATTACT     1200

CCAACTATAT TATAAAGCTT AAATAAGAGG CCGTGTTAAT TAGTACTTGT TGCCTTTTGC     1260

TTTATGGTGT TGTTTATTAT GCCTTGTATG CTTGTAATAT TATCTAGAGA ACAAGATGTA     1320

CTGTGTAATA GTCTTGTTTG AAATAAAACT TCCAATTATG ATGCAAAAAA AAAAAAAA      1379
```

(2) INFORMATION FOR SEQ ID NO:3:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:3:

```
GGGGTCTAGA ATTCGTNAAY ACNATHATHT AYAAYGT                                37
```

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:4:

```
GGRTCYTTYG CYTCRTT                                                     17
```

(2) INFORMATION FOR SEQ ID NO:5:

(i) SEQUENCE CHARACTERISTICS:
        (A) LENGTH: 35 base pairs

```
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:5:

GGGGTACCAG ATCTGAAGGG AAGATGAAGT CGATG                               35

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:6:

GGGGTACCAG ATCTGACGAA GTCGATGCTT GTGG                                34

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

GGGCCCGGGA AGCTTTATAA TATAGTTGG                                      29

(2) INFORMATION FOR SEQ ID NO:8:

(i) SEQUENCE CHARACTERISTICS:
        (A) LENGTH: 597 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

TCATCAAAAT ATTTAGCAGC ATTCCAGATT GGGTTCAATC AACAAGGTAC GAGCCATATC    60

ACTTTATTCA AATTGGTATC GCCAAAACCA AGAAGGAACT CCCATCCTCA AAGGTTTGTA   120

AGGAAGAATT CTCAGTCCAA AGCCTCAACA AGGTCAGGGT ACAGAGTCTC CAAACCATTA   180

GCCAAAAGCT ACAGGAGATC AATGAAGAAT CTTCAATCAA AGTAAACTAC TGTTCCAGCA   240

CATGCATCAT GGTCAGTAAG TTTCAGAAAA AGACATCCAC CGAAGACTTA AAGTTAGTGG   300

GCATCTTTGA AAGTAATCTT GTCAACATCG AGCAGCTGGC TTGTGGGGAC CAGACAAAAA   360

AGGAATGGTG CAGAATTGTT AGGCGCACCT ACCAAAAGCA TCTTTGCCTT TATTGCAAAG   420

ATAAAGCAGA TTCCTCTAGT ACAAGTGGGG AACAAAATAA CGTGGAAAAG AGCTGTCCTG   480

ACAGCCCACT CACTAATGCG TATGACGAAC GCAGTGACGA CCACAAAAGA ATTCCCTCTA   540

TATAAGAAGG CATTCATTCC CATTTGAAGG ATCATCAGAT ACTAACCAAT ATTTCTC     597
```